United States Patent
Thompson

(10) Patent No.: US 9,228,975 B2
(45) Date of Patent: Jan. 5, 2016

(54) PATIENT SERUM/PLASMA SAMPLE RESISTIVITY FOR ELECTROLYTE RESULT VERIFICATION

(75) Inventor: David R. Thompson, Kennett Square, PA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 139 days.

(21) Appl. No.: 14/344,645

(22) PCT Filed: Aug. 24, 2012

(86) PCT No.: PCT/US2012/052317
§ 371 (c)(1),
(2), (4) Date: Mar. 13, 2014

(87) PCT Pub. No.: WO2013/039672
PCT Pub. Date: Mar. 21, 2013

(65) Prior Publication Data
US 2015/0008122 A1 Jan. 8, 2015

Related U.S. Application Data

(60) Provisional application No. 61/533,886, filed on Sep. 13, 2011.

(51) Int. Cl.
*G01N 27/06* (2006.01)
*G01N 27/416* (2006.01)
*G01N 33/49* (2006.01)

(52) U.S. Cl.
CPC .............. *G01N 27/416* (2013.01); *G01N 27/06* (2013.01); *G01N 27/4166* (2013.01); *G01N 33/49* (2013.01)

(58) Field of Classification Search
CPC ...................................................... G01N 27/06
See application file for complete search history.

(56) References Cited

U.S. PATENT DOCUMENTS

| 4,686,479 A | 8/1987 | Young |
| 5,004,583 A | 4/1991 | Guruswamy et al. |

(Continued)

FOREIGN PATENT DOCUMENTS

| EP | 0 213 343 A2 | 3/1987 |
| EP | 2 479 562 A1 | 7/2012 |

(Continued)

OTHER PUBLICATIONS

Extended European Search Report dated Feb. 17, 2015 of corresponding European Patent Application No. 12832397.9, 3 Pages.

(Continued)

*Primary Examiner* — Evan Pert
(74) *Attorney, Agent, or Firm* — Pepper Hamilton LLP

(57) ABSTRACT

Verification of patient sample electrolyte results using a separate quantitative measurement of sample resistivity. Sample resistivity may be used to measure small differences in resistivity of one sample to the next, and in comparison to a standard solution, in order to verify the results of sample electrolyte measurements being measured at the same time by, for example, individual ion selective electrodes (ISE) in a clinical analyzer. Providing a separate or secondary quantitative means for verification of the measured results of sample electrolytes using sample resistivity solves the problem of electrolyte result variability in sample electrolyte measurements. The process may compare a measured sample resistivity to an expected resistivity value as a verification of the accuracy of individual electrolyte results. Suspect samples—e.g., where the electrolyte resistivity results do not fit the expected resistivity—may be flagged. This separate verification step provides added confidence in the measured electrolyte results and can identify when problems occur or interferences are present in real time.

23 Claims, 22 Drawing Sheets

(56) References Cited

U.S. PATENT DOCUMENTS

| | | | |
|---|---|---|---|
| 5,134,359 | A | 7/1992 | Durley et al. |
| 5,971,933 | A | 10/1999 | Gopakumaran et al. |
| 6,339,334 | B1 | 1/2002 | Park et al. |
| 7,426,408 | B2 * | 9/2008 | DeNuzzio ............ A61B 5/14532 600/345 |
| 7,917,202 | B2 * | 3/2011 | Chamney ............ A61B 5/0537 600/506 |
| 2003/0120462 | A1 | 6/2003 | Yundt-Pacheco |
| 2004/0015063 | A1 * | 1/2004 | DeNuzzio ............ A61B 5/14532 600/347 |
| 2005/0126929 | A1 | 6/2005 | Mansouri et al. |
| 2005/0177038 | A1 * | 8/2005 | Kolpin ............... A61B 5/04284 600/372 |
| 2006/0025661 | A1 | 2/2006 | Sweeney et al. |
| 2011/0000796 | A1 | 1/2011 | Situ et al. |
| 2015/0008122 | A1 * | 1/2015 | Thompson ............ G01N 33/49 204/403.01 |

FOREIGN PATENT DOCUMENTS

| | | |
|---|---|---|
| WO | 02/08902 A1 | 1/2002 |
| WO | 2011/002907 A1 | 1/2011 |
| WO | 2011/034168 A1 | 3/2011 |

OTHER PUBLICATIONS

Beckman Coulter, Actionable information and intelligent connections in real time, REMISOL Advance Clinical Information Systems, Dec. 2010 [retrieved on Oct. 19, 2012]. Retrieved from the Internet<URL: http://beckmancoulterclinis.com/pdf/REMISOL_Whitepaper.pdf> p. 7.

PCT International Search Report and Written Opinion dated Nov. 13, 2012 (7 Pages).

* cited by examiner

PATIENT SERUM/PLASMA SAMPLE RESISTIVITY FOR ELECTROLYTE RESULT VERIFICATION

CROSS-REFERENCE TO RELATED APPLICATIONS

This application claims priority to U.S. provisional application Ser. No. 61/533,886 filed Sep. 13, 2011, which is incorporated herein by reference in its entirety.

TECHNOLOGY FIELD

The present invention relates generally to sample electrolyte result verification, and more particularly to use of a measurement of patient sample (e.g., blood serum and plasma) resistivity for electrolyte result verification in a clinical analyzer.

BACKGROUND

All known higher life forms require a subtle and complex electrolyte balance between the intracellular and extracellular milieu. In particular, the maintenance of precise osmotic gradients of electrolytes is important for good health. Such gradients affect and regulate the hydration of the body as well as blood pH, and are critical for nerve and muscle function. Various mechanisms exist in living species that keep the concentrations of different electrolytes under tight control. Serious electrolyte disturbances, such as dehydration and over hydration, may lead to cardiac and neurological complications and, unless they are rapidly resolved, may result in a medical emergency.

For these reasons, instruments exist for the analysis of patient samples for diagnosis purposes. For example, the measurement of electrolytes is a commonly performed diagnostic procedure. Electrolytes measured most often include sodium ($Na^+$), potassium ($K^+$), and chloride ($Cl^-$). One known method for measuring electrolytes is potentiometric measurement of ions using individual sensors employing ionophores to selectively attract the ion of interest. For example, an ion selective electrodes (ISE) measurement of sodium ($Na^+$), potassium ($K^+$), and chloride ($Cl^-$) electrolytes is performed by the V-LYTE® IMT Module of the Dimension Vista® Integrated System manufactured by Siemens Healthcare Diagnostics Inc. of Newark, Del.

A problem with conventional sample electrolyte measurement systems is electrolyte result variability and these conventional systems do not provide a separate or secondary quantitative means for verification of the measured results of an electrolyte measuring module on, for example, a clinical chemistry analyzer. This may lead to errors or inaccurate results since conventional systems and methods do not provide a means to detect errors in individual result calculations that could be caused by, for example, electrical or chemical interferences in the ISE measurements.

Some conventional systems attempt to address this problem by monitoring the output of the individual ISE sensors and setting limits for electrical voltage drift that may occur when interferences are present. Also, simple tests for the presence or absence of sample may be performed to check for gross positioning errors. These techniques, however, do not provide a second or separate quantitative means for verification of the calculated results of a sample electrolyte measurement.

What is needed is a separate quantitative verification process that can detect or flag suspect samples where the measured electrolyte results do not fit the expected electrolyte results as determined by this separate quantitative means.

SUMMARY

Embodiments of the present invention address and overcome one or more of the above shortcomings and drawbacks, by providing devices, systems, and methods for providing a separate measurement of a blood serum or plasma sample resistivity for the purpose of verifying the electrolyte results that are being measured at the same time by individual ion selective electrodes (ISE), for example. Sample resistivity is commonly used to verify the presence of liquid or air in the ISE. Currently, sample resistivity is not used for any other purpose. It has been discovered that sample resistivity can also be used to measure small differences in resistivity of one sample to the next, and in comparison to a standard solution (e.g., a solution having a known composition and concentration of components) in order to verify the results of sample electrolyte measurements (e.g., ion concentrations in the sample).

Embodiments of the present invention are directed to verification of patient sample electrolyte results using a separate quantitative measurement of sample resistivity. Providing a separate or secondary quantitative means for verification of the measured results of sample electrolytes using sample resistivity solves the problem of electrolyte result variability in sample electrolyte measurements. The process may compare a measured sample resistivity to an expected resistivity value as a verification of the accuracy of individual electrolyte results. Suspect samples—e.g., where the electrolyte resistivity results do not fit the expected resistivity—may be flagged. This separate verification step provides added confidence in the measured electrolyte results and can identify when problems occur or interferences are present in real time.

According to one embodiment of the invention, a sample resistivity measurement system is provided for sample electrolyte result verification. The sample resistivity measurement system may include a sample cartridge for performing sample electrolyte measurements. The sample cartridge may include one or more ion selective electrodes, a common reference electrode to provide a constant reference potential, a circuit connecting each of the one or more ion selective electrodes with the reference electrode, and an electrometer connected to the circuit to measure a potential of the one or more ion selective electrodes against the reference electrode. Concentrations of desired ions may be calculated from an electrode voltage difference between a sample having an unknown ion concentration and an unknown resistivity and a standard solution having a known ion concentration and a known resistivity. This calculation provides a measured sample electrolyte result. In a flow through sample cartridge configuration, the sample and the standard solution may be run alternately in series through the sample cartridge to obtain necessary measurements. The sample resistivity measurement system allows for measurement of a sample resistivity and a standard solution resistivity, which may be used to establish a response slope for the one or more ion-selective electrodes and to provide a reference point against which the sample may be compared. A resistivity ratio may be calculated from the measured sample resistivity of the sample and the measured sample resistivity of said standard solution. Historical data comprising measured sample electrolyte concentrations and/or measured sample resistivities may be obtained and an expected sample resistivity response may be developed from this historical data. A tolerance about the expected sample resistivity response may be developed based on experience and generally accepted data. The measured sample electrolyte result may be verified as an acceptable result if the measured sample resistivity falls within the tolerance about the expected sample resistivity response.

According to one aspect of the invention, the measured sample electrolyte result may be flagged as an unacceptable result if the measured sample resistivity do not correlate with an expected result (or theoretical result), or when measured results are outside an acceptable tolerance or range about the expected result. A sample measurement flagged as unacceptable may result in one or more actions, including: retry the measurement; purge and cycle the sample fluid and then make new measurement; generate an error; record an error; retry the measurement; indicate an alarm; flag the result; initiate an automated recovery (e.g., priming and/or cleaning), etc.

According to another aspect of the invention, the ion-selective electrodes may include one or more of: a sodium (Na) electrode, a potassium (K) electrode, and a chlorine (Cl) electrode; for measuring one or more desired ions comprising: sodium (Na), potassium (K), and chlorine (Cl), respectively.

According to another aspect of the invention, the sample comprises patient serum and plasma samples and includes a measurement of: sodium (Na) ions and potassium (K) ions; to verify an electrolyte measurement of sodium (Na) and potassium (K).

According to another aspect of the invention, the sample comprises patient serum and plasma samples and includes a measurement of: sodium (Na) ions, potassium (K) ions, and chlorine (Cl) ions; to verify an electrolyte measurement of sodium (Na), potassium (K), and chlorine (Cl).

According to another aspect of the invention, the sample comprises patient serum and plasma samples and includes a measurement of: sodium (Na) ions and potassium (K) ions; and sodium (Na) ions, potassium (K) ions, chlorine (Cl) ions; to isolate and verify an electrolyte measurement of chlorine (Cl).

According to another aspect of the invention, a relationship between electrolyte concentration and resistivity may be represented by a ratio of the measured sample resistivity over the measured standard solution resistivity, which provides a power relationship between electrolyte concentration and resistivity.

According to another aspect of the invention, a relationship between electrolyte concentration and resistivity may be represented by a ratio of the measured standard solution resistivity over the measured sample resistivity, which provides a linear relationship between electrolyte concentration and resistivity.

According to another embodiment of the invention, a method for verifying patient sample electrolyte results using patient sample resistivity measurements is provided. The method comprises:

providing a sensor cartridge comprising:
one or more ion-selective electrodes;
a common reference electrode to provide a constant reference potential;
a circuit connecting each of the one or more ion-selective electrodes with the reference electrode;
an electrometer connected to the circuit to measure a potential of the one or more ion-selective electrodes against the reference electrode;
running a patient sample through the sensor cartridge;
measuring a concentration of a desired ion in the patient sample using one or more ion-selective electrodes;
measuring a resistivity of the patient sample using an electrometer connected to the circuit connecting the one or more ion-selective electrodes and the reference electrode, wherein the electrometer measures a potential of the one or more ion-selective electrodes against the reference electrode;
running a standard solution through the sensor cartridge;
measuring a concentration of the desired ion in the standard solution using the one or more ion-selective electrodes;
measuring a resistivity of the standard solution to calibrate a slope response of the one or more ion-selective electrodes and to provide a reference point against which the patient sample is compared;
calculating a concentration of the desired ion from the comparison of the measured concentration of the desired ion in the patient sample and the measured concentration of the desired ion in the standard solution;
calculating a resistivity ratio comprising the measured patient sample resistivity divided by the measured standard solution resistivity;
comparing the measured patient sample resistivity to an expected resistivity developed from historical resistivity measurements of other patient samples; and
flagging the measured patient sample if the measured patient sample resistivity ratio does not fall within a predefined tolerance about the expected resistivity ratio.

According to another aspect of the invention, the method comprises:
plotting a summation of ions along an x-axis and the resistivity ratio along a y-axis;
plotting an expected sample resistivity response curve comprising the historical resistivity measurements;
plotting a tolerance curve using the predefined tolerance, the tolerance curve plotted about the expected sample resistivity response curve; and
plotting the measured sample resistivity relative to the expected sample resistivity response curve and the tolerance curve.

The systems and methods provide a separate and quantitative means for verification of measured sample electrolyte results of an electrolyte measuring module on a clinical chemistry analyzer. For example, one embodiment includes: an integrated multi-sensor technology (IMT) having ion selective electrodes (ISE). A sample cartridge may be inserted in the IMT for receipt and measurement of the sample and the standard solution. A database storing historical data of measured sample electrolyte concentrations is provided and may be accessed by a processor connected to the IMT to perform calculations of ion concentrations and to determine whether the measured sample resistivity falls within the predefined tolerance.

This technology is particularly well suited for, but by no means limited to, use with clinical analyzers, such as the Dimension VISTA® clinical analyzer manufactured by Siemens Healthcare Diagnostics Inc. of Newark, Del.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

Figure 1:
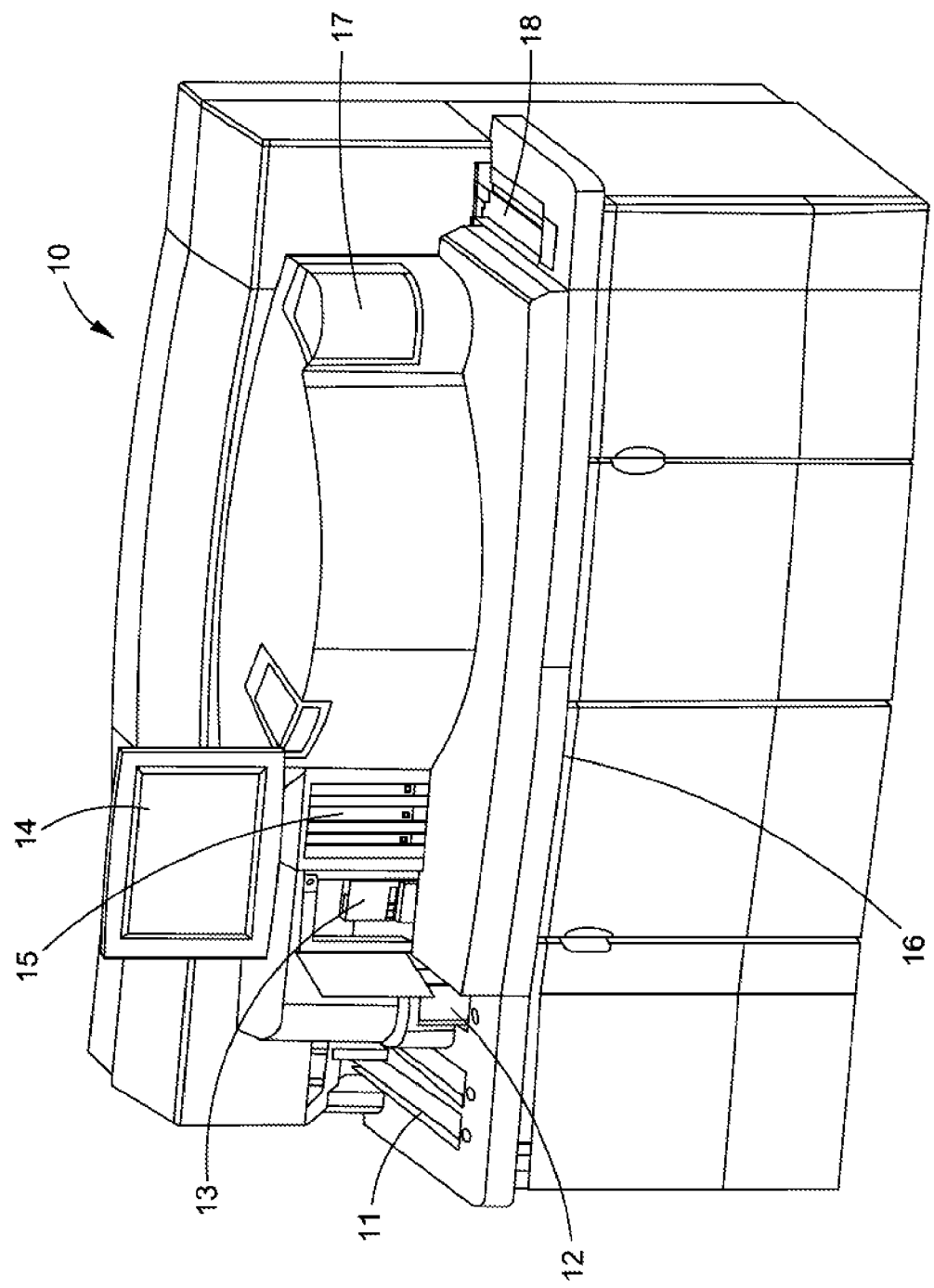
FIG. 1 is a perspective view of an exemplary diagnostic instrument in which the sample resistivity for electrolyte result verification may be employed.

Embodiments of the present invention solve the problem of electrolyte result variability in sample electrolyte measurements by providing a separate quantitative means for verification of the measured results of, for example, an electrolyte module on a clinical chemistry analyzer using sample resistivity. As used herein, the terms "module," "analyzer," and "instrument" include, but are not limited to, any clinical analyzer that incorporates the measurement of electrolytes. Embodiments of the present invention provide a verification means of the electrolyte results by comparing a measured sample resistivity to an expected resistivity value. Expected resistivity values may be based on, for example, historical data of measured/observed electrolyte concentrations. This historical data for different samples may be collected and stored from instruments in the field, normalized using a resistivity ratio, and plotted and averaged together to determine an expected result curve for that sample. This comparison of measured to expected sample resistivity can serve as a verification of the accuracy of individual electrolyte results. This sample electrolyte result verification process can flag suspect samples where the electrolyte resistivity results do not fit the expected resistivity. Sample resistivity provides a means for identification of sample measurements that are producing incorrect electrolyte results to trigger a flag or corrective action.

Errors or inconsistencies in sample electrolyte measurements may occur, for example, if there are interfering substances in the sample like drugs or preservatives which impact the ion selective electrode (ISE) sensor membrane adversely, causing drifts in potential. Sample resistivity for electrolyte result verification may be used to detect interfering substances. Embodiments of the present invention using sample resistivity for sample electrolyte verification may also pick up problems with small micro-bubbles or poor fluid flow through the ISE, which can adversely impact the measured sample electrolyte results.

According to one embodiment of the invention, the sample resistivity for an electrolyte result verification process utilizes a resistivity detect circuit to quantify the resistivity of the sample fluid in relation to a standard fluid—e.g., a Standard A fluid. As used herein, a standard is a calibrator-type solution having a know quantity of certain components that may be run to calibrate the sensors and to compare an unknown sample to a test. A standard may be used to calibrate the slope response of the sensors between high and low. For example, for every unknown sample that is run, it may be followed with a Standard solution (e.g., Standard A). In operation, an unknown sample is run followed by a known—i.e., a Standard; and then an unknown sample is run followed by a known; and then a comparison may be performed of the difference between the unknown sample and known Standard to calculate the electrolyte concentration of the unknown sample.

The resistivity detect circuit may be an existing a liquid/air detection circuit of an ISE sensor or a new a liquid/air detection circuit. The measured resistivity is directly proportional to the ionic content of the sample and allows the measured or calculated results to be compared to the expected resistivity. This then provides a separate quantitative measurement of the sample to confirm the electrolyte concentrations that were measured by the ISE sensors. This separate verification step provides added confidence in the measured electrolyte results and can be used to identify when problems occur or interferences are present in real time (e.g., substantially immediately).

In one exemplary embodiment of this concept, the sample liquid readings over a predetermined time period (e.g., 24 hours) are compared to the Standard A liquid readings. In this example, one might expect to observe a positive bias of roughly about 10 mV. The reason for this is that the resistivity of the average patient sample is very consistent and is slightly higher than Standard A solution. As such, embodiments of the present invention allow detection of a problem on each individual sample. Therefore, the automatic sample resistivity for electrolyte result verification process can prevent many erroneous sample electrolyte results from being reported before detection of a problem or interference.

The invention may be realized in several embodiments. For example, one embodiment for serum and plasma samples may include the measurement of Na and K to verify Na, K. For example, another embodiment for serum and plasma samples may include the measurement of Na, K, and Cl to verify Na, K, and Cl. For example, another embodiment for serum and plasma samples may include the measurement of Na and K, and Na, K and Cl to isolate and verify Cl. For example, alternative embodiments of this concept may include the use of other analytes measured in the calculation of the ionic strength of the sample (e.g., Calcium, Magnesium, uric acid, Urea, Glucose, Ammonia, and others). These additional analytes may be necessary for accurate analysis of urine samples, for example. For serum and plasma samples, the Na and K concentrations dominate the ionic strength. Therefore, Na+K and/or Na+K+Cl are preferred when testing serum and plasma samples. These elements typically produce reliable and consistent results since serum and plasma comprise a very finite range for Na, K, and Cl and there are very few other sources of conductive elements.

One exemplary use for sample resistivity for electrolyte result verification may be in an in vitro diagnostic instrument 10 (see FIG. 1) intended to duplicate manual analytical procedures such as pipetting, mixing, heating, and measuring spectral intensities to determine a variety of analytes in human body fluids. One such suitable instrument is the Dimension Vista® system manufactured by Siemens Healthcare Diagnostics Inc. of Newark, Del.

FIG. 1 shows an exemplary diagnostic instrument 10 in which the process for sample resistivity for electrolyte result verification may be employed. As shown in FIG. 1, the diagnostic instrument includes, for example: sample rack lanes 11; STAT input lane 12; integrated multi-sensor technology (IMT) system 13; display device (e.g., touch screen monitor) 14; reaction vessel loader 15; user input device (e.g., keyboard and mouse) 16; cuvette loader 17; and reagent loader 18. The diagnostic device illustrated in FIG. 1 may perform multiple operations, including assay measurement.

Figure 2:
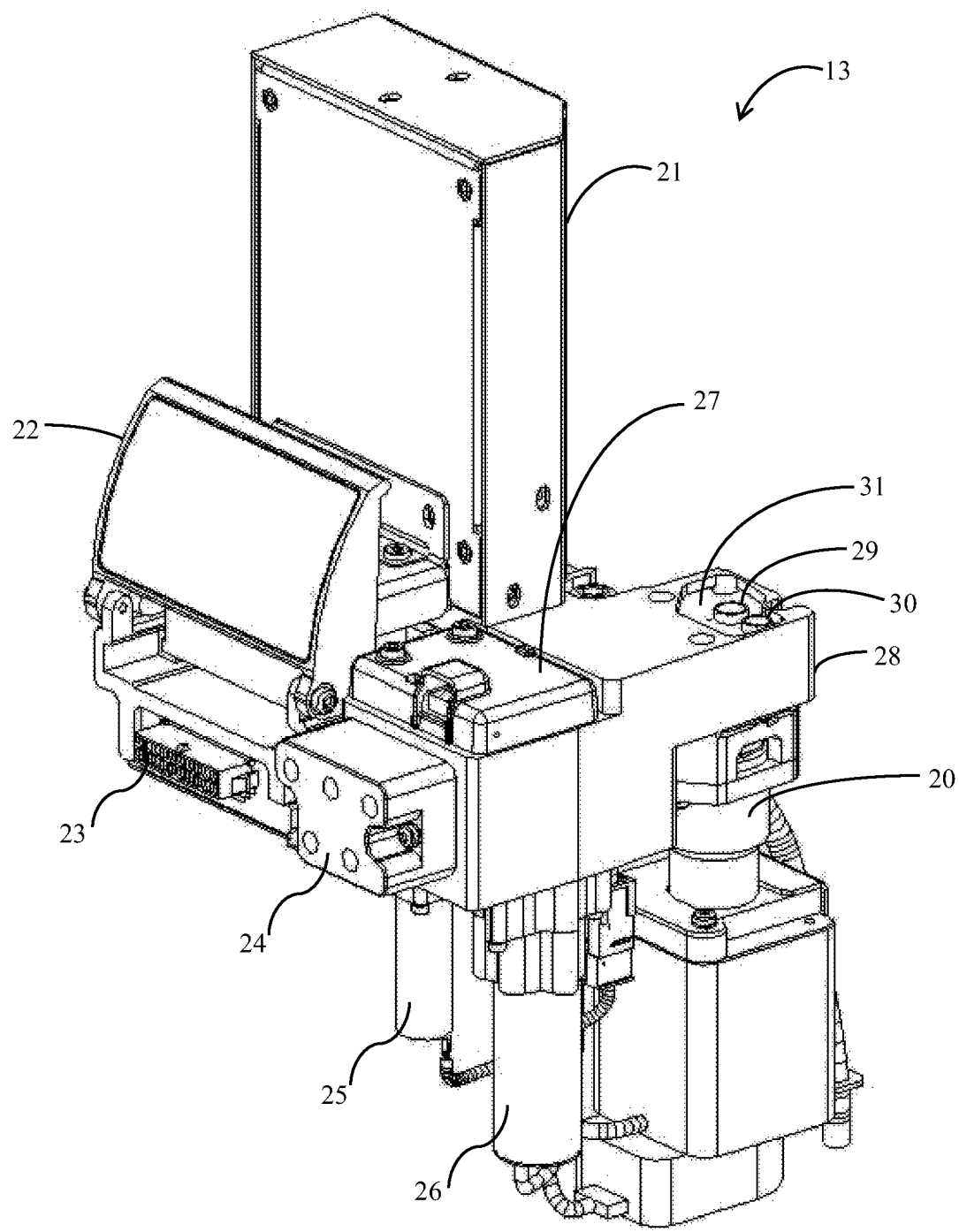
FIG. 2 is a perspective view of an exemplary integrated multi-sensor technology (IMT) module that is part of the diagnostic instrument of FIG. 1.

Measurement of electrolytes (e.g., sodium ($Na^+$), potassium ($K^+$), chloride ($Cl^-$)) may be performed in the IMT system 13 (see FIG. 2). The IMT system 13 on the exemplary diagnostic device 10 provides for the potentiometric determination of sodium, potassium, and chloride using a flow-through sensor cartridge 40 enclosing electrolyte sensors (e.g., solid-phase electrodes) (see FIGS. 5 and 6). When an electrolyte test is requested, the IMT sampler probe (not shown) aspirates sample from an aliquot plate and dispenses it into the IMT port on a manifold where a dilution of the sample with a diluent is made using a fluid "chase" method. The pre-diluted, bulk, fluid standard solutions may be supplied to the sensors through a rotary shear valve 20 with fluid ports for conveying, for example, Standard A (Std-A), Standard B (Std-B), Sample, and Air. The sample port may be rinsed with Std-A solution, for example, between samples. The diluted sample is then pulled through the IMT sensor 40 for measurement. The IMT probe may be rinsed after each aspirate-dispense action.

In one application, the IMT system 13 processes all samples to obtain desired results. One goal of the exemplary diagnostic device IMT system 13 is to provide a robust system for rapidly processing high volumes of fluid samples, such as serum, plasma and urine samples.

The exemplary IMT system 13 uses four primary solutions—including Standard A, Standard B, Salt Bridge, and Diluent—in its sample processing. The primary purpose of Standards A and B is to establish the response slope of the Na, K, and Cl electrodes and to provide a reference point against which the sample is compared. The salt bridge may be pumped to the reference channel of the sensor cartridge 40 to provide a constant reference potential at the reference electrode and a renewable liquid junction potential. The IMT system 13 may include a Diluent, which may be used to dilute samples to a desired ratio. The IMT system 13 may also include a Dilution Check, which may comprise an aqueous solution of known concentration of Na, K, and Cl that may be processed as a normal sample to validate and correct the system dilution ratio.

Further details of the exemplary IMT system 13 are shown and described in more detail with reference to FIG. 2. As shown in FIG. 2, the IMT system 13 includes an electrolyte reader assembly 21, an actuator chip placement door 22, a module electrical cable connector 23, a fluids interface manifold 24, a 2-way solenoid valve 25, a solenoid pump 26, a pressure manifold 27, a manifold assembly 28, and rotary shear valve 20 mounted to the manifold assembly 28. The manifold 28 includes a sample port 29 and a vent port 30. The manifold 28 also has a fluid overflow retention area 31, also referred to as the "moat." The moat 31 may be drained by a small diameter parasitic port (not shown) that connects to the main waste channel of the manifold 28. The sensor cartridge 40 is received by the IMT system 13 by opening placement door 22 and inserting the sensor cartridge 40.

Figure 3:
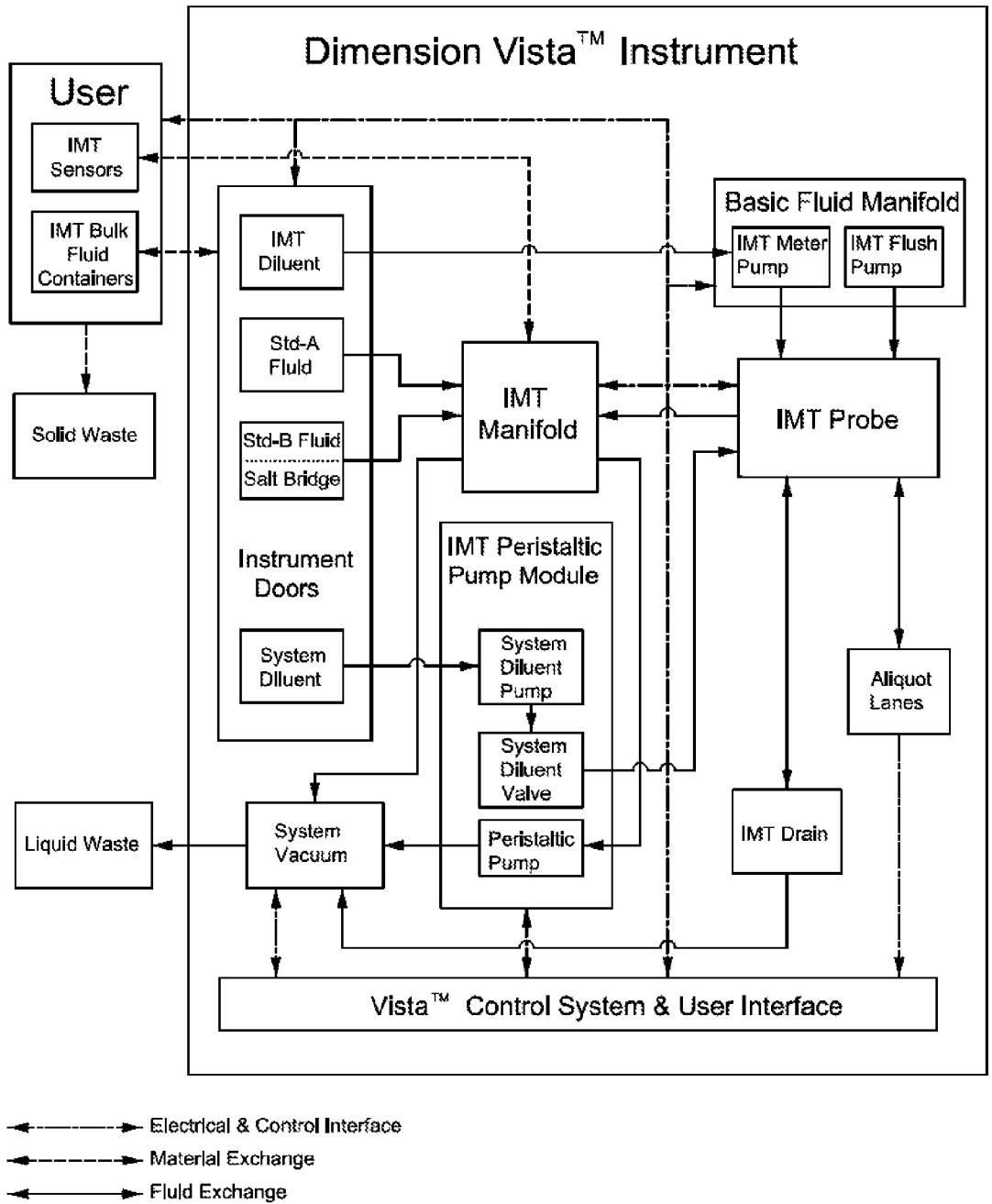
FIG. 3 illustrates an exemplary IMT system functional interface block diagram.
Figure 4:
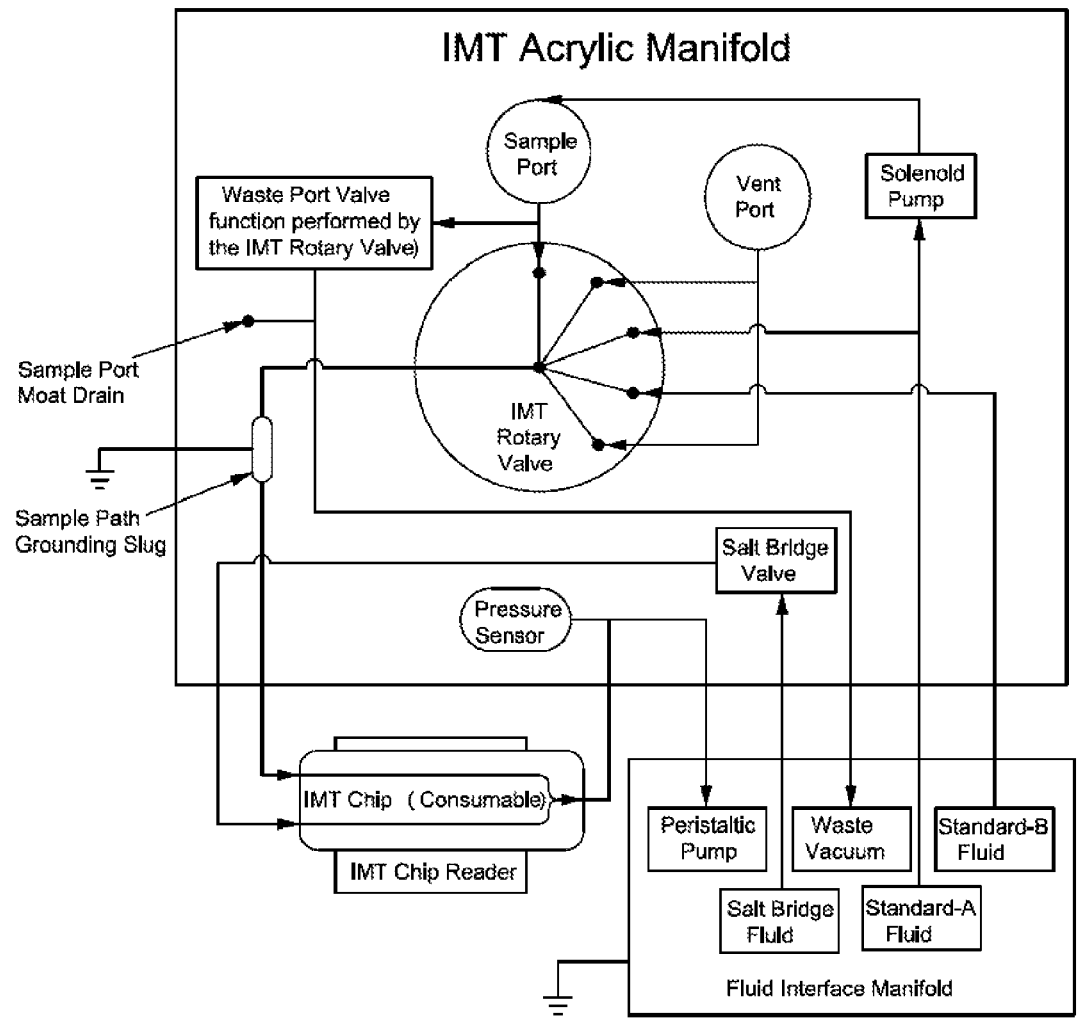
FIG. 4 illustrates an exemplary IMT system fluidic schematic.

FIG. 3 illustrates an exemplary IMT system 13 functional interface block diagram and FIG. 4 illustrates an exemplary IMT module fluidic schematic. As shown, the IMT manifold 28 provides the fluidic channels for the Standard A and Standard B, Salt Bridge, vent air, sample fluids, and liquid waste. The IMT manifold 28 supports the fluidic hardware used to control the routing of fluids through the manifold 28. In one embodiment, the manifold 28 comprises an acrylic plastic having internal pathways. A stainless steel fluid grounding pin (not shown) may be imbedded in the acrylic to provide an electrical ground to fluid in the sample channel. Threaded inserts, locating pins, and the IMT fluid pins are included.

During sample/standards processing, the fluids are selectively directed to the sample pathway and into the IMT sensor cartridge sample channel with the rotary shear valve 20. Fluids are drawn into the manifold 28, for example, with vacuum pressure created by a peristaltic pump module or a vacuum waste system. Air segments in the fluid streams are introduced by momentarily moving the rotary shear valve 20 to a vent location to access ambient air. Standard A solution is pumped by the Standard A solenoid pump into the sample port in aliquots to rinse the sample port. In the illustrated embodiment, Standard A is the only fluid moved within the manifold 28 using positive pressure. The flow rate of the Standard A flush is regulated by the diameter of the outlet path from the Standard A flush pump. A salt bridge solenoid valve allows salt bridge solution to enter the salt bridge channel of the IMT sensor cartridge 40.

The IMT rotary valve may include a stepper controlled ceramic rotary shear valve 20 in accordance with one embodiment of the present invention. The main fluidic components of the valve are a highly polished ceramic rotor and stator (not shown). The rotor and stator are forced together by a compression spring that pushes against a thrust bearing (not shown). In the exemplary embodiment, the rotor has two slots: the selector slot; and the waste slot. Also in the exemplary embodiment, the stator has seven fluid ports, including: center or common port; sample port; vent 1 port; Standard A port; Standard B port; vent 2 port; and a waste port. Fluids are directed from one stator port to another by positioning the slots in the rotor to connect the desired stator ports.

Figure 5:
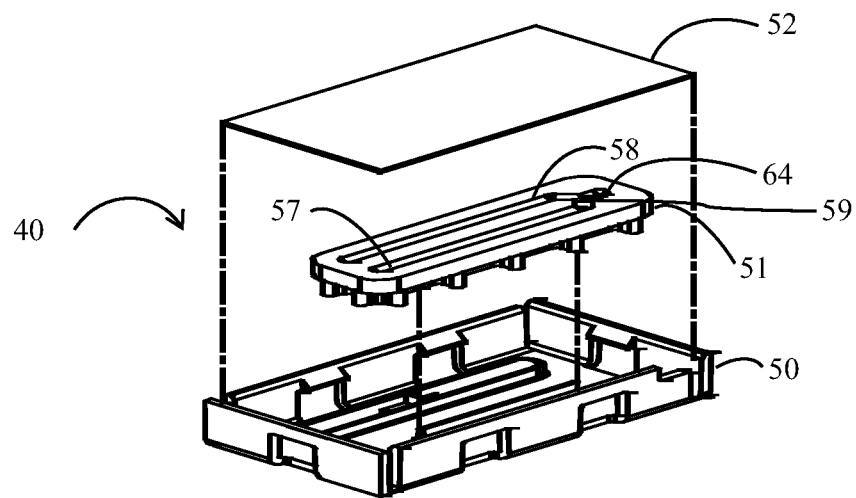
FIG. 5 is an exploded perspective view of an exemplary ISE sensor cartridge.
Figure 6:
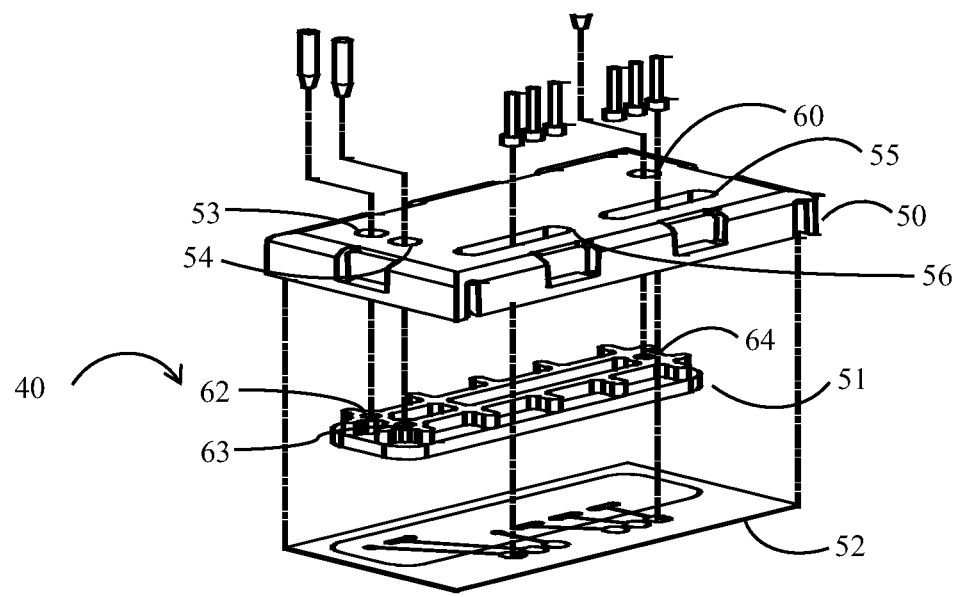
FIG. 6 is a reverse exploded perspective view of the exemplary sensor cartridge of FIG. 5.
Figure 7:
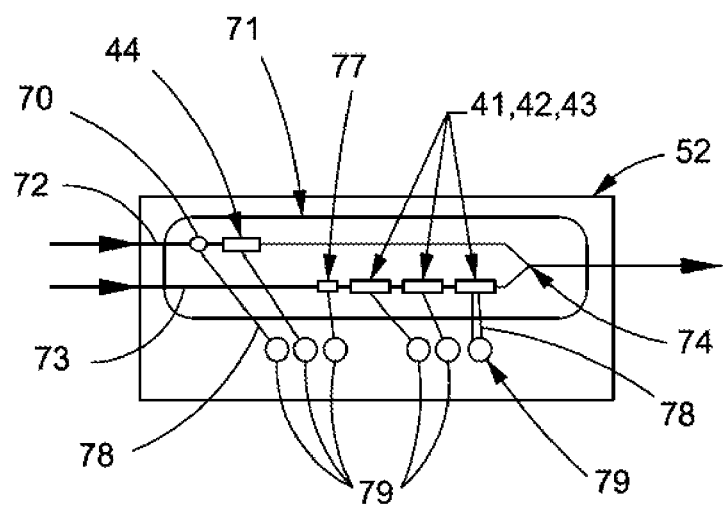
FIG. 7 is a plan view of an exemplary sensor substrate that may be used in the sensor cartridge of FIG. 5.

The IMT system 13 design may include a sensor cartridge 40 including the sensors for the measurement of sodium, potassium, chloride and a common reference electrode (see FIGS. 5-7). At equilibrium, an electrical potential is generated that is proportional to the logarithm of the analyte concentration in the sample. The potential of the sodium, potassium, and chloride electrodes is amplified and measured sequentially against the reference electrode by, for example, a high impedance electrometer. The reference electrode may include a chloride sensing membrane coupled to a silver chloride electrode. The reference electrode is in contact, and in equilibrium with, Salt Bridge Solution. The Nernst equation is used to calculate the concentration of the desired ion from the electrode voltage difference between Standard-A and the sample:

$$C_{sample} = C_{standard} \times 10^{(\Delta E/slope)}$$ [Nernst Equation]

where:
$C_{sample}$=ion concentration in the sample.
$C_{standard}$=ion concentration in the standard.
$\Delta E$=difference (in millivolts) between the electrode potential of the sample and the standard.
Slope=calibration slope (in millivolts/decade).

The sensor cartridge 40 is presented to the primary fluidic processing module, a single, multi-layer acrylic manifold and electrometer, summarily identified is the "IMT Manifold" 13. All sample processing operations (dilution, fluid selection, transport and measurement) are performed within this unit.

In an exemplary IMT sample measurement cycle, the peristaltic pump positions the sample fluid in the instrument sensor cartridge 40 where the sodium, potassium, and chloride ions reach equilibrium with their respective electrode membrane surface.

An exemplary sensor cartridge 40 is shown in FIGS. 5-7. In the illustrated embodiment, the sensor cartridge 40 is an ion selective electrode assembly having a reference element and a plurality of sensor elements (e.g., electrodes) linearly positioned in parallel on a substrate for use in a clinical analyzer. As shown, the sensor cartridge 40 includes Na, K, Cl and reference electrodes 41, 42, 43, 44, respectively (see FIG. 7). The sensor cartridge 40 also includes a detection circuit 77 capable of detecting a change in impedance in the sample fluid stream due to, for example, the presence of fluid and/or air and is also capable of detecting resistivity of the sample.

As shown in FIGS. 5-7, the sensor cartridge 40 may further include a housing 50, a fluid channel membrane 51, and a sensor substrate 52. The housing 50 may comprise a plastic material having fluid inlet ports for reference 53 and sample 54, a fluid outlet opening 60, and one or more openings 55, 56 for allowing electrical connectors to pass through the housing 50. Snaps (not shown) on the housing 50 engage the peripheral edge of the substrate 52 to hold the elastomer fluid channel membrane 51 in compression when assembled.

As shown in FIGS. 5-7, the fluid channel membrane 51 may comprise an elastomer flow channel that is in contact with an inside surface of the housing 50. As shown, the fluid channel membrane 51 includes two substantially parallel grooves forming a reference channel 57 and a sample channel 58 that combine at a liquid junction 59. When assembled with the substrate 52, the grooves form fluid channels 57, 58. Inlet openings for reference 62 and sample 63 are provided at a first end of the fluid channel membrane 51 and are aligned with the inlet openings 53, 54 of housing 50. An outlet opening 64 is provided at a second end of fluid channel membrane 51 downstream of the liquid junction 59. The outlet opening 64 is aligned with fluid outlet opening 60 of housing 50. Reference and sample fluids enter the sensor cartridge 40 through inlet openings for reference 62 and sample 63, are drawn through the respective flow channels 57, 58, come together at the liquid junction 59 downstream of the sensor elements, and exit the sensor cartridge 40 via outlet opening 64.

As further shown in FIGS. 5-7, the sensor substrate 52 may comprise a ceramic material and includes a reference input and a sample input. The sensor substrate 52 includes a circuit 70 disposed on the substrate 52. A dielectric 71 is also provided on the substrate 52. The circuit 70 is laid out on the substrate 52 to correspond to the fluid channels and includes a reference channel 72, a sample channel 73, and a liquid junction 74. The substrate 52 includes a reference electrode 44 on the reference channel 72. The substrate 52 also includes electrodes 41, 42, 43 (corresponding to Na, K, Cl) on the sample channel 73. The substrate 52 may also include an air/fluid detection circuit 77. The air/fluid detection circuit 77 acts as a resistivity circuit. Traces 78 on the substrate 52 connect the electrodes 41, 42, 43, 44 to conductors 79. When installed in an IMT system 13, contact pins (not shown) extend through the housing 50 to make an electrical connection to the conductors 79 to an IMT reader.

Additional details of the sensor cartridge may be found in U.S. Pat. No. 5,284,568, entitled Disposable Cartridge For Ion Selective Electrode Sensors, which is herein incorporated by reference in its entirety.

Figure 8:
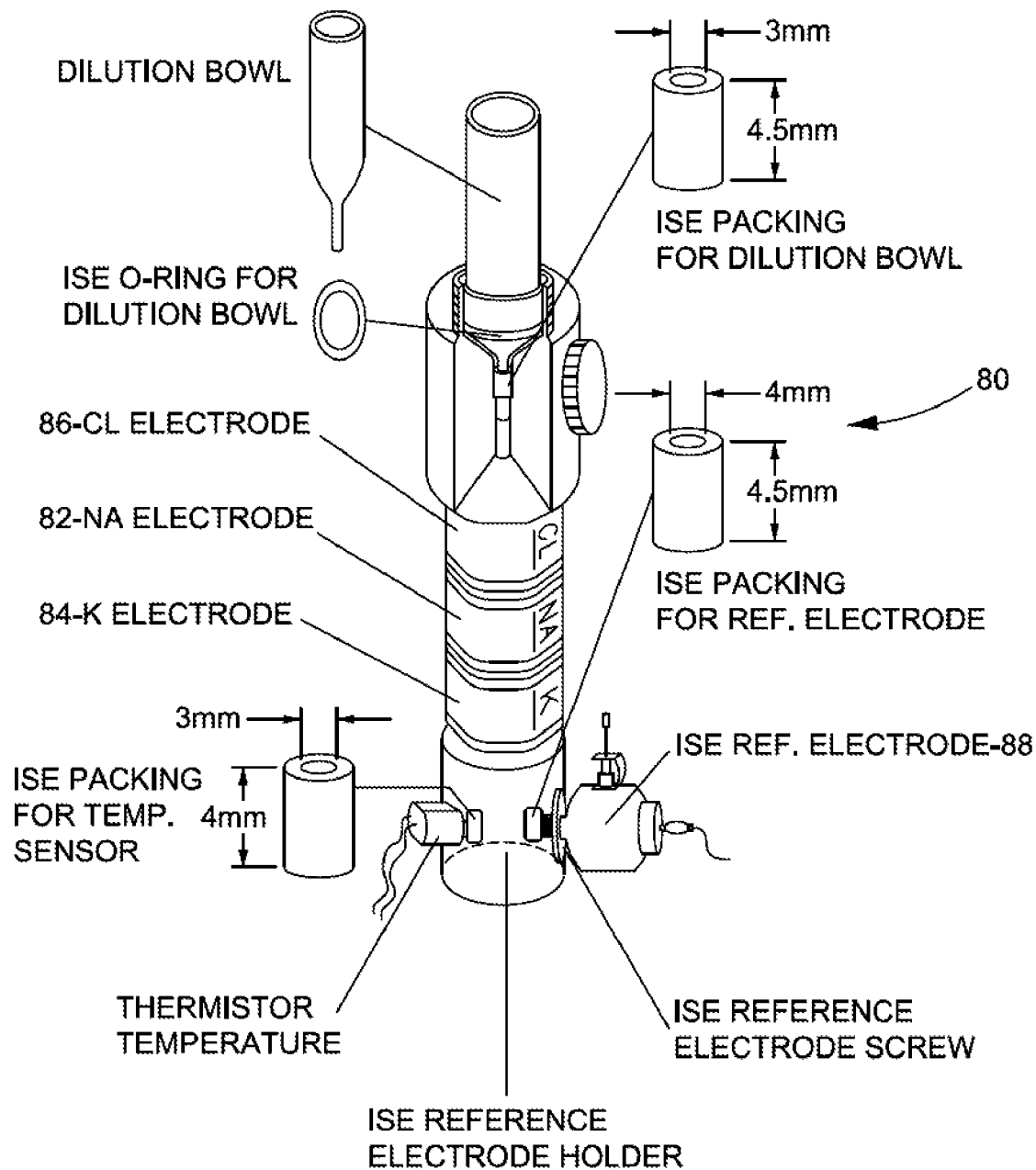
FIG. 8 is a view of another exemplary ISE sensor having a stacked configuration.

FIG. 8 shows another exemplary ion-selective electrode (ISE) potentiometric sensor 80. The sensor 80 shown in FIG. 8 includes a stacked electrode configuration. In this embodiment, the Na and K electrodes 82, 84 may comprise crown ether membranes, the Cl electrode 86 may comprise a superlayer solid molecule orientation membrane, and the reference electrode 88 may comprise an AG/AgCl electrode.

The IMT system may include a PCA IMT measure assembly. In one embodiment, the PCA IMT measurement assembly has an input impedance of the potentiometric amplifiers of $\geq 10^{12}$ ohms. Input noise per amplifier may be less then 20 µV, and each may have a gain of 8, over an input range of +/−312 mV. The amplifiers measure the reference voltage of the IMT sensor cartridge 40, as well as, the Na, K, Cl channels.

Figure 9:
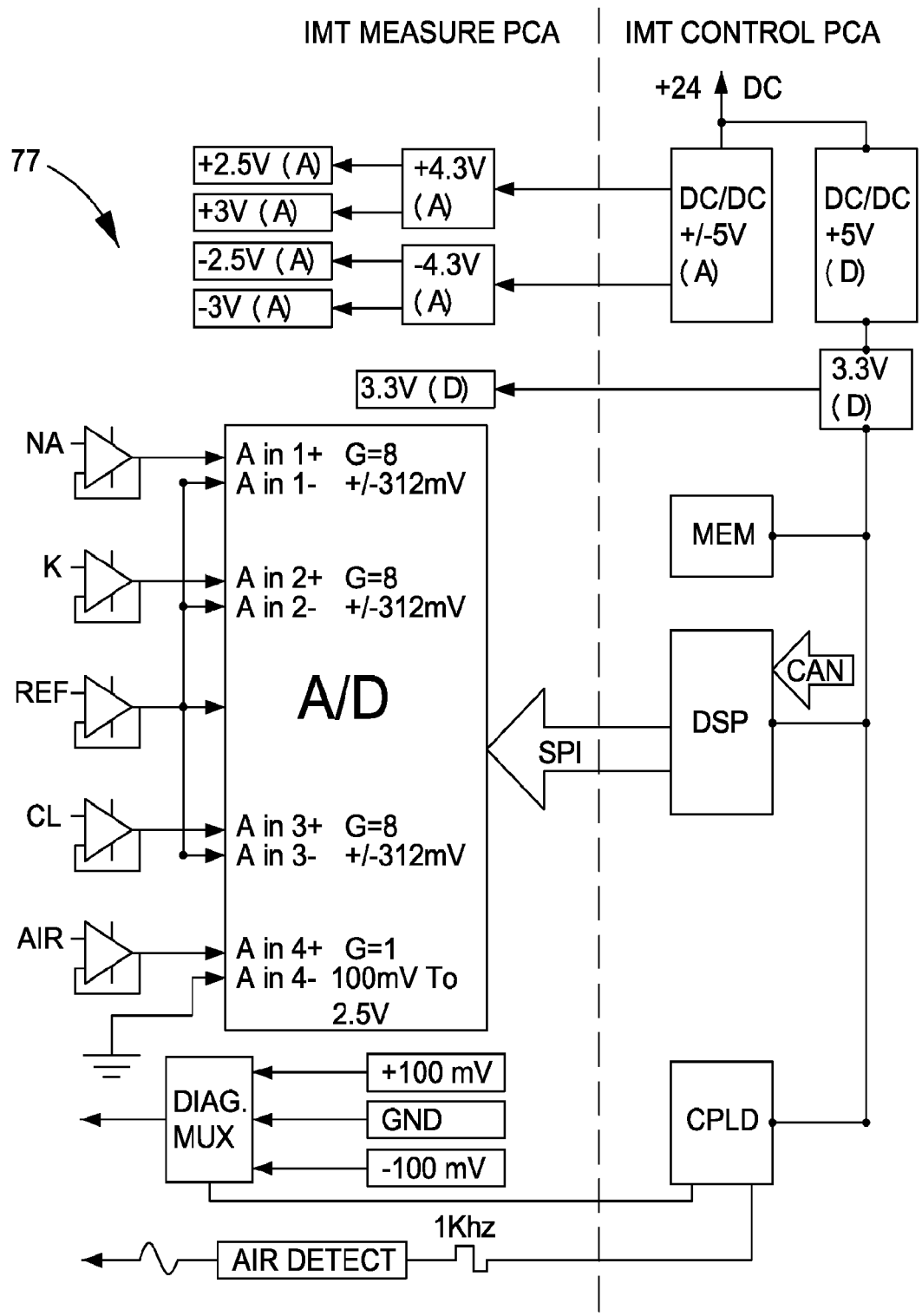
FIG. 9 is a schematic of exemplary IMT measurement and control circuitry.

As shown in FIG. 9, the board also includes a detection circuit 77 capable of detecting a change of impedance in the sample fluid stream due to the presence of fluid or air and the resistivity of the sample. The output of the detection circuit will depend upon the fluid stream distance, conductance, and resistivity. The output voltage for air detected is greater then the voltage developed by the presence of fluid. In some embodiment, the nominal output voltage of the detection circuit 77, with Standard A in place, is a positive DC voltage of approximately 250 mv. The operational range may be from 100 mV to +2.25V. The air/fluid detection circuit 77 may have a settling time of approximately 50 milliseconds (5 time constants). The potentiometric circuits may have a settling time of approximately 1.3 seconds.

In some embodiments, the potentiometric biosensors make use of ion-selective electrodes 41, 42, 43 in order to transduce the biological reaction into an electrical signal. The electrical potential is determined at very high impedance allowing effectively zero current flow and causing no interference with the reaction. The voltage generated at the sensor may be buffered through a unity gain amplifier and amplified by an internal PGIA of an A/D. The signal may be digitized and the data/value may be transmitted via an SPI interface to the IMT control board, and then sent to a host computer (not shown) via a CAN interface. The host computer converts the value to a concentration of the tested biological sample.

As shown in FIG. 9, the IMT reader 21 (also referred to as electrometer) may include a CAN communication addressable element of the instrument distributed control system. Upon command from the host computer via the CAN bus, input voltages to the high-impedance inputs of the IMT reader are passed through a unity gain buffer, differentially compared with the output of the Reference Electrode, amplified (e.g., 8×), and converted to a digital value using a A/D converter. The values are transmitted within the reader via an SPI serial data/control bus to the controlling DSP. The DSP returns the data in a command response to the system controller. The IMT reader 21 may be positioned on top of the IMT manifold 28 so that spring-loaded contact pins align with conductive pads on the surface of the ceramic sensor cartridge 40 to measure the electrical output (e.g., voltage) of the ion sensors (e.g., electrodes) 41, 42, 43.

The IMT reader 21 may generate a fluid detect AC waveform that is injected across the input end of the sample channel 73 and the ground terminal at the entrance of the salt bridge channel 72. The reader measures the voltage across the two channels 70, 77. The more conductive (lower resistance) the contents of the channel, i.e. with salty fluid present, the lower the air detect voltage reading. Standard-A typically reads about 250 mV. Air in the channel increases the resistance, decreases current flow, and causes a higher voltage reading (air typically measures approximately 1300-1450 mV). Commands received through the CAN Communication Bus provide instructions on when and how to perform the measurements. The software has been designed to request multiple (e.g., 5) readings of each of the Na, K, and Cl channels for each measurement request. Each channel is read once; Na then K and then Cl. This sequence is repeated for as many times as are requested and as rapidly as the readings can be made. Each reading may be time-stamped so that a drift adjustment can be made, if necessary.

In a clinical analyzer, Sample and Standard may be measured not only for Na, K, and Cl but also for resistivity (e.g., liquid detect). As a general rule, as the salt content of a sample increases, the resistivity decreases. Embodiments of the present invention provide a verification process for electrolyte results by checking resistivity of the sample and comparing the measured resistivity to a theoretical or expected resistivity based on the actual historical electrolyte ion concentrations measurements.

In one embodiment, the IMT Module electrometer also has an impedance measurement circuit which injects a signal (e.g., a 1 KHz, 0.7 V (peak to peak) sine wave) into the sample channel 73 and measures the resistance to the sensor ground in the reference channel. This measurement is the basis of the air and liquid detection, but also can measure the relative ionic concentration of the sample.

The following may represent the relationship between Electrolyte Concentration and Resistivity Ratio:

$$\text{Resistivity Ratio} = \frac{\text{Sample Fluid Resistivity}}{\text{Std A Resistivity}} = \frac{\text{Fluid Verify}}{\text{Std A Liquid}}$$

wherein electrolyte concentration=(Na+K+CL) or (Na+K).

Figure 10:
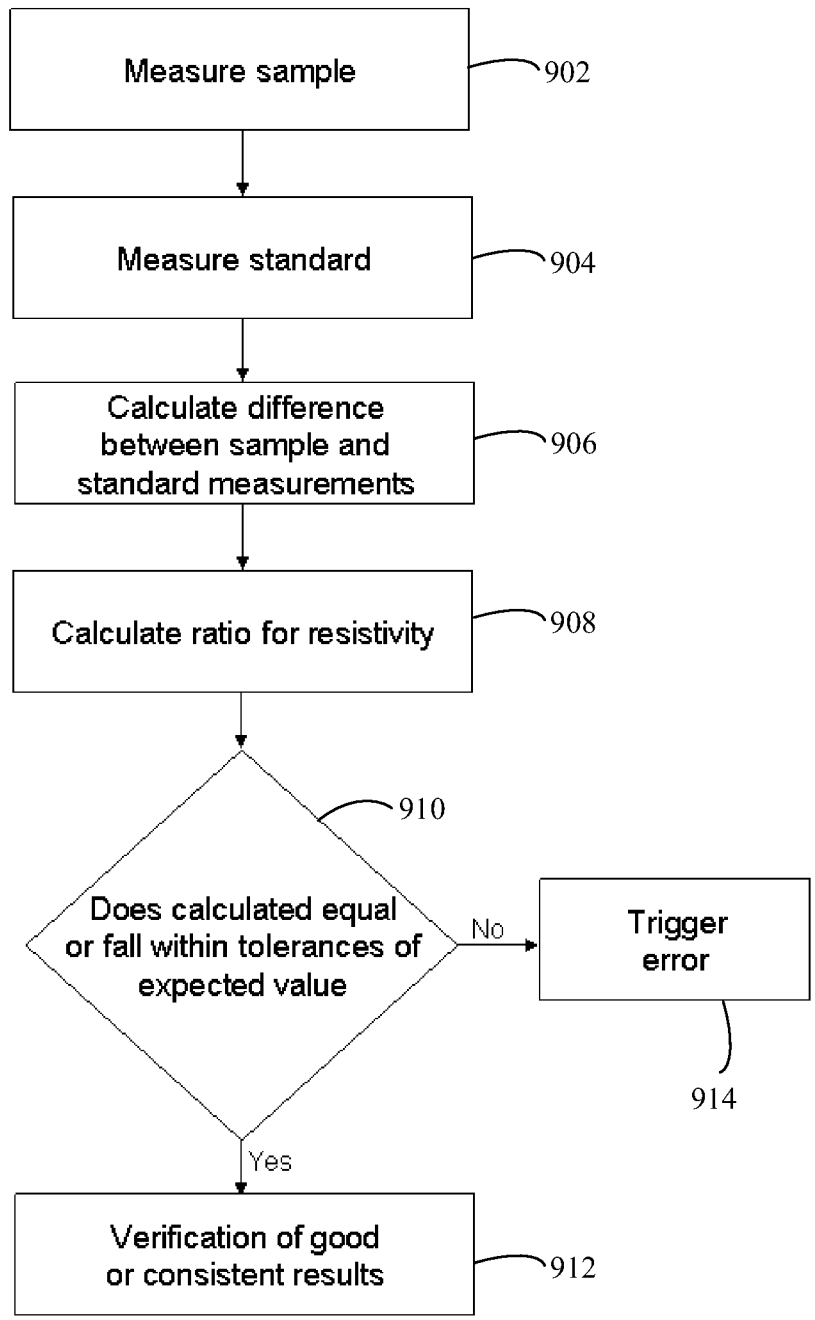
FIG. 10 is a flowchart showing exemplary logic for verification of electrolyte results using patient sample resistivity measurements.

FIG. 10 shows an exemplary process 900 for using sample resistivity for electrolyte result verification. As shown in FIG. 10, the process begins with a sample measurement, step 902, and a measurement of a standard, step 904. These measurements include the voltage output for each sensor (Na, K, Cl) relative to a reference and the resistivity. At step 906, the process calculates the difference between the relative voltages for each sensor and the concentration of Na, K, Cl, for example, using the Nernst equation. At step 908, a ratio of the resistivity is calculated. A comparison of the calculated or measured resistivity to an expected resistivity is made at step 910. If the measured resistivity matches the expected resistivity, or falls within an acceptable tolerance (e.g., an upper and lower limit), then the sample electrolyte results are verified at step 912. If the measured resistivity does not match the expected resistivity, or falls outside acceptable tolerances (e.g., an upper and lower limit), then the sample electrolyte results are flagged at step 914. The flagged results may trigger one or more actions.

FIGS. 11-23 show examples of both laboratory testing and field testing of use of sample resistivity for electrolyte result verification. FIGS. 11-23 show that a better correlation is achieved when using only the Na+K value for ion concentration. This is likely because the majority of the cations come from Na and K. CL is the anion for both of them and, as a result, does not represent significant additional ionic strength. Using the resistivity ratio normalizes all measurements to the concentration of Standard A at the time of measurement on the specific instrument.

The plots of FIGS. 11-23 include the summation of ions (mmol/L) along the x-axis and the ratio of two resistivity voltages (mV) for Sample fluid and Standard fluid along the y-axis. FIGS. 11-17 show the data fit to a power equation ($y=mx^b$) illustrating a best fit of the data. FIGS. 18-23 show the data fit to a linear equation (y=mx+b). Also shown in each plot is $R^2$ which illustrates the goodness of the fit ratio. The closer $R^2$ is to one, the better the fit. $R^2=1$ indicates a perfect fit.

Figure 11:
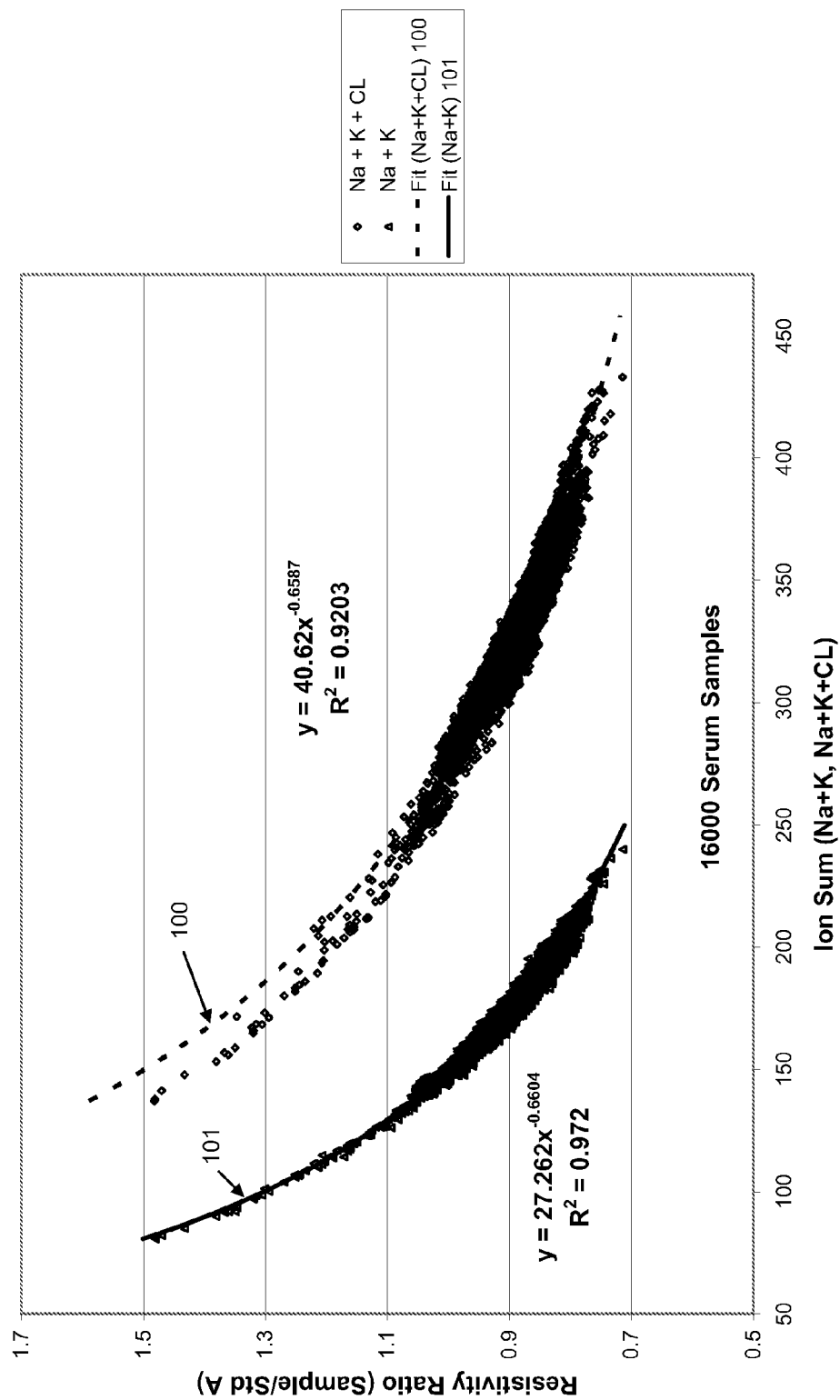
FIG. 11 is a plot showing an exemplary resistivity measurement.

FIG. 11 is a plot of the electrolyte result verification for 16,000 serum samples. As shown in FIG. 11, the ion summation is plotted versus the resistivity ratio of the serum samples for a lab instrument. As shown, the ion summation includes Na+K and NA+K+CL. In each case, the plots show good correlation of the data about the power fit lines—e.g., power fit (Na, K, CL) (line 100) and power fit (Na, K) (line 101).

Figure 12:
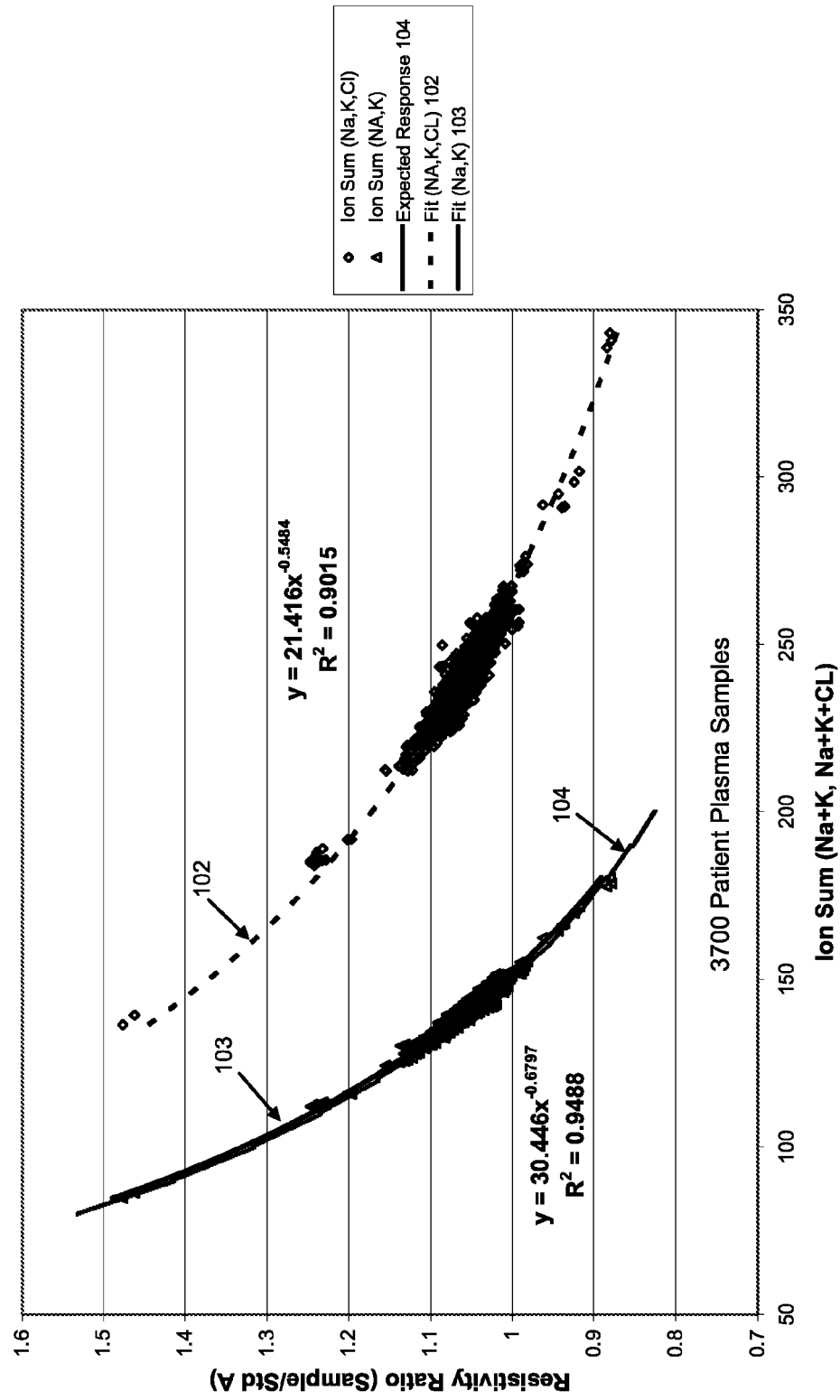
FIG. 12 is a plot showing an exemplary resistivity measurement.

FIG. 12 is a plot of the electrolyte result verification for 3,700 patient samples. As shown in FIG. 12, the ion summation is plotted versus the resistivity ratio of the patient samples for an operational instrument in the field. As shown, the ion summation includes Na+K and NA+K+CL. In each case, good correlation of the data about the power fit lines is illustrated—e.g., power fit (Na, K) (line 103) and fit (Na, K, CL) (line 102). The expected response curve is depicted by dashed line 104, which corresponds well with the fit for Na, K. As describe earlier, the expected response curve may be determined from historical data observed over multiple instruments and samples.

Figure 13:
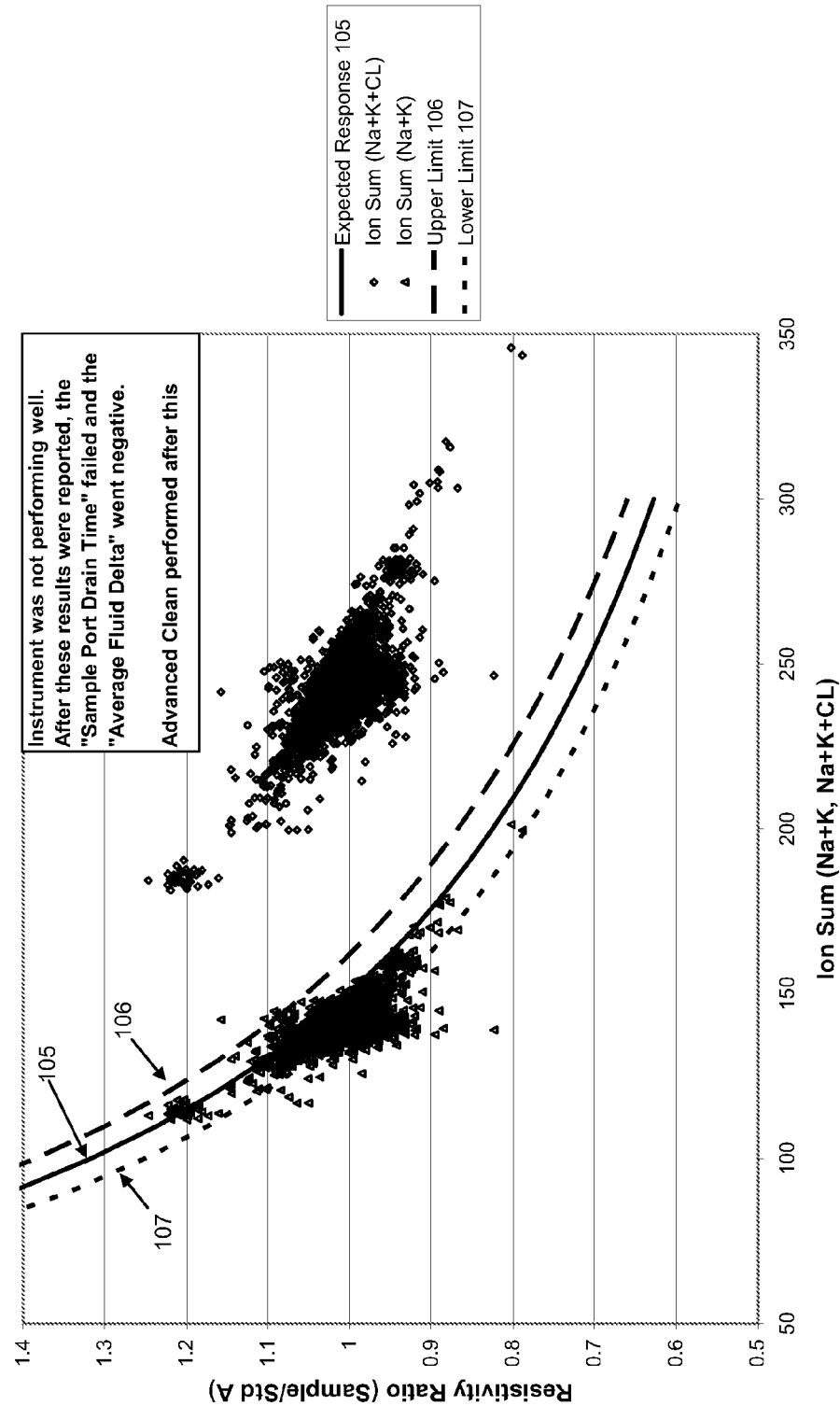
FIG. 13 is a plot showing an exemplary resistivity measurement.

FIG. 13 is a plot of the electrolyte result verification for patient samples. As shown in FIG. 13, the ion summation is plotted versus the resistivity ratio of the samples for another operational instrument in the field. As shown, the ion summation includes Na+K and NA+K+CL. In this example, there is not good correlation of the measured data to the expected response (line 105). As shown, ion sum (Na+K) is not well grouped and certain readings fall outside the upper limit (shown by dashed line 106) and the lower limit (shown by dashed line 107) about the expected response (line 105). This example shows that the instrument is not performing well (i.e., not performing as expected) and that corrective action may be necessary. For example, in the illustrated example, the "sample port drain time" failed and the "average fluid delta" went negative shortly after the results were reported. This is a sign of possible buildup, flow restrictions, or clogs in the sample port. In this example, advanced cleaning of the electrolyte module was indicated.

Figure 14:
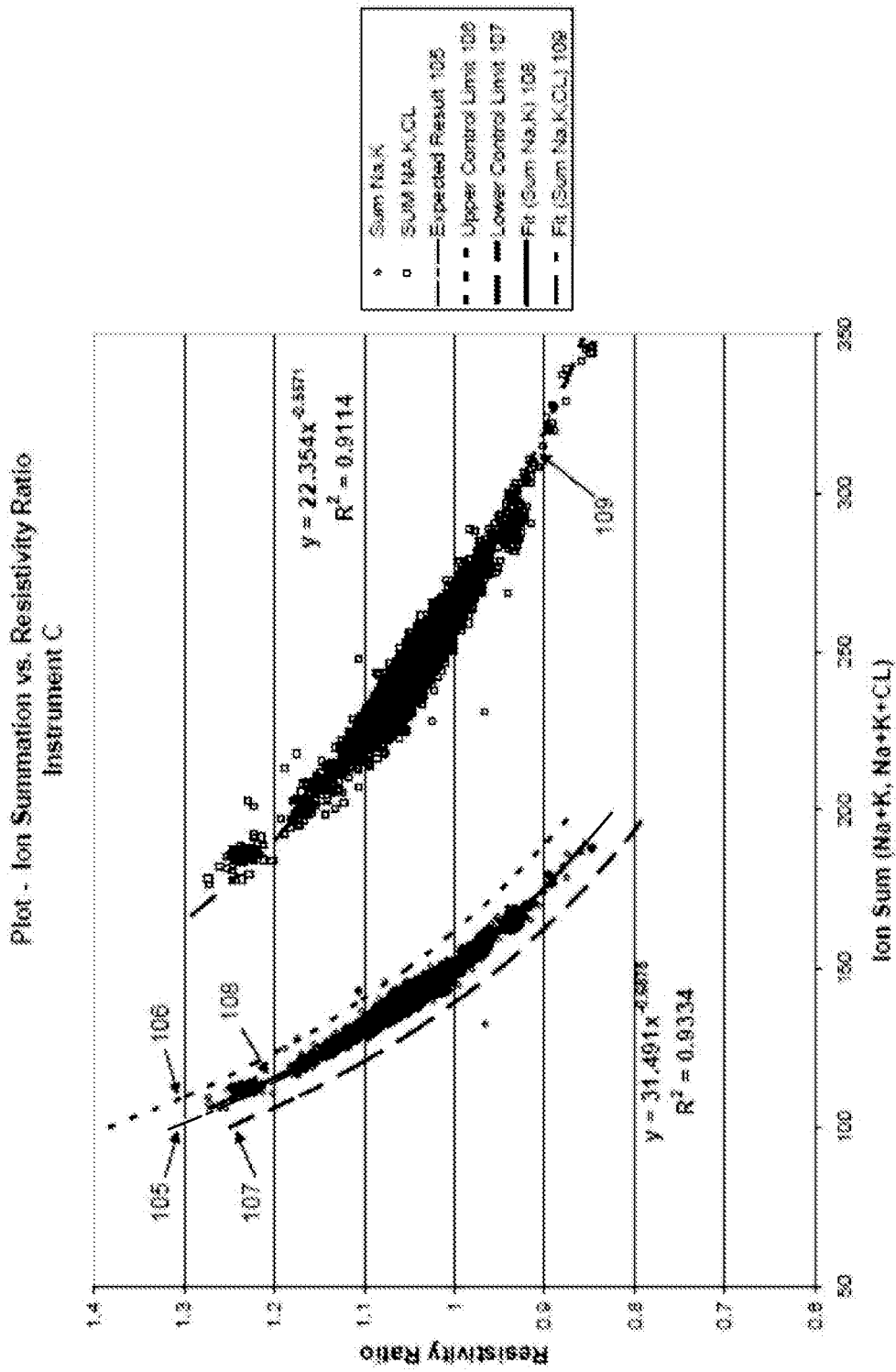
FIG. 14 is a plot showing an exemplary resistivity measurement.

FIG. 14 is a plot of the electrolyte result verification for the same patient samples and instrument as FIG. 13 taken after advanced cleaning of the instrument was performed. As shown in FIG. 14, the plot of ion summation versus the resistivity ratio of the samples now shows good correlation. As shown, the ion sum Na+K is now well grouped about the expected response (shown by line 105) and the power fit (shown by line 108) and within the upper limit (shown by dashed line 106) and the lower limit (shown by dashed line 107). Also, the ion summation for NA+K+CL indicated good correlation about the power fit (sum Na, K, CL) (shown by line 109).

Figure 15:
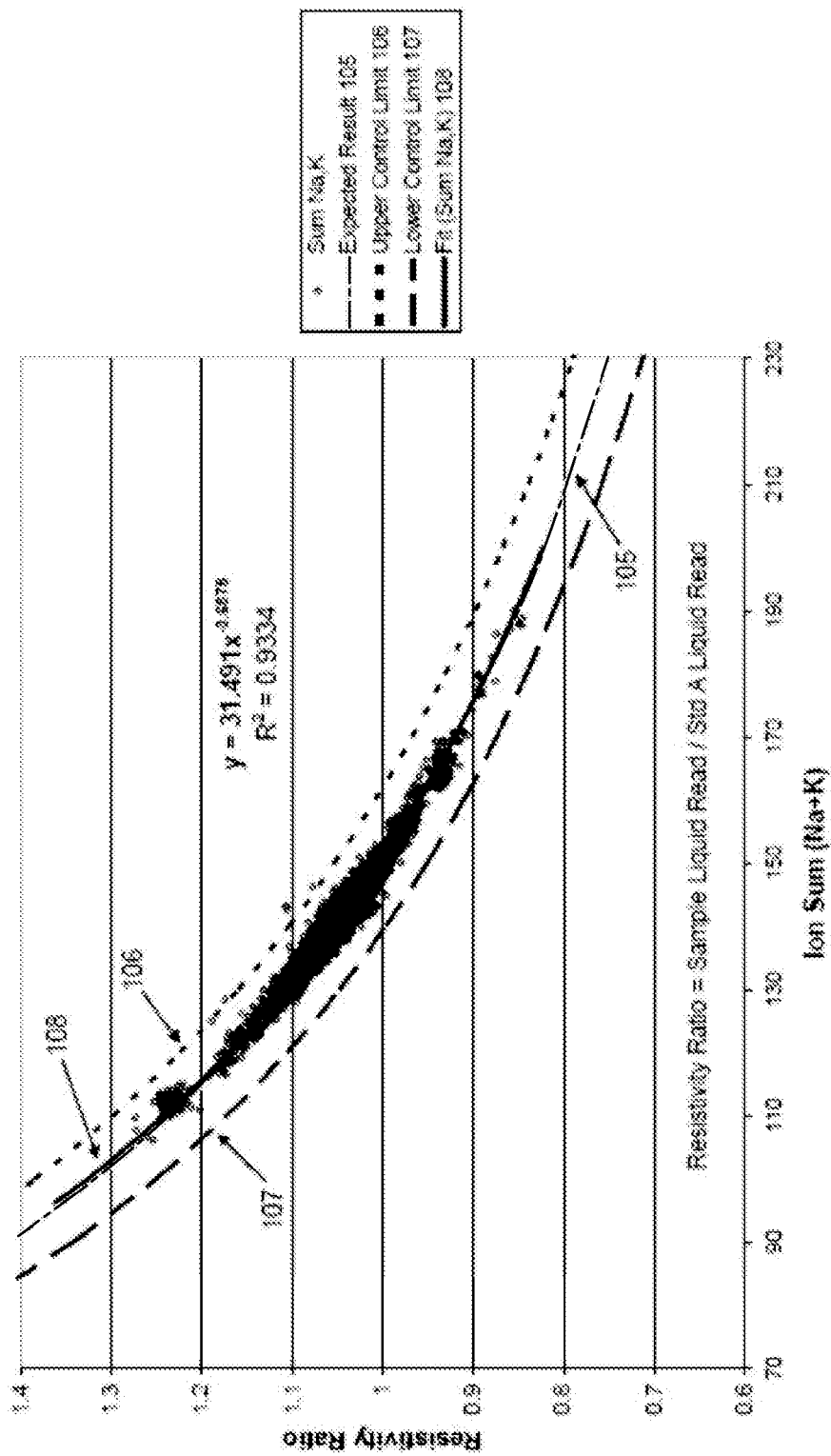
FIG. 15 is a plot showing an exemplary resistivity measurement.

FIG. 15 is a more detailed plot of the electrolyte result verification for the ion sum Na+K of FIG. 14. As shown in FIG. 15, the ion sum (Na+K) scale has been changed to show additional detail.

Figure 16:
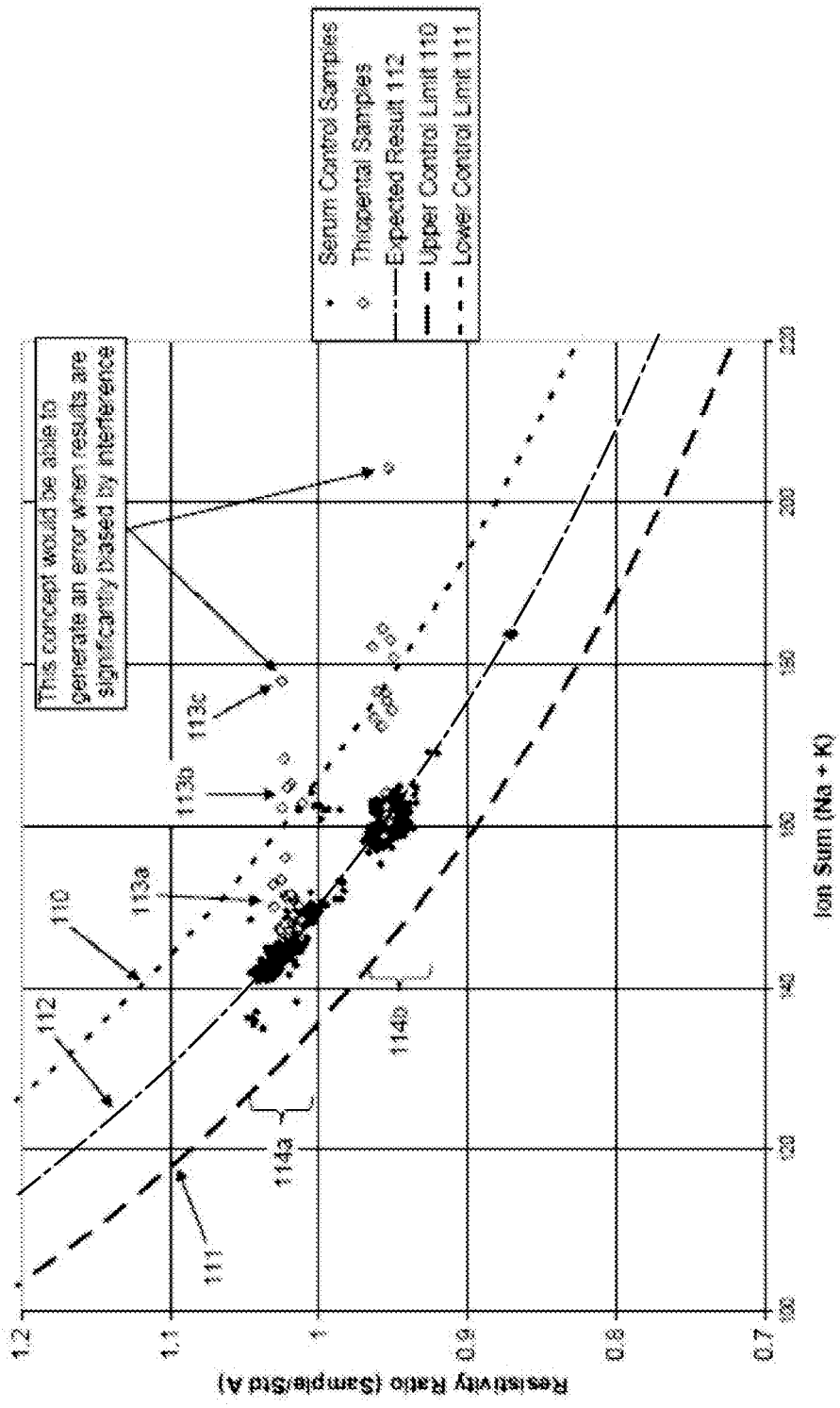
FIG. 16 is a plot showing an exemplary resistivity measurement.

FIG. 16 shows the results of drug interference testing on a lab instrument for serum control samples and, in this example, samples containing increasing concentrations of thiopental. The sample resistivity for electrolyte result verification would allow generation of a measurement error when results are significantly biased by interference. For example, when measurements are outside of an upper control limit (shown by line 110) and a lower control limit (shown by line 111) of an expected result (shown by line 112). As shown, the testing included serum control samples and serum samples spiked with Thiopental. Two serums were run (represented by 114a, 114b) and three concentrations of Thiopental were run (shown by sample groupings 113a, 113b, and 113c). Increasing concentrations were in the order of 113a, 113b, 113c, and as illustrated in the plot, the higher the concentration of Thiopental the further the drift to the right (and further from the expected response) the results. At some point, the drug interference may cause the results to be outside of the established control limits.

Other known interfering substances for electrolytes for Sodium include: Thiopental @ 7 mg/dl, Iron @ 1 gm/dl, Benzylalkonium Cl—@ 3 mg/dl. Other known interfering substances for electrolytes for Potassium include: Iron @ 1 gm/dl, Benzylalkonium Cl—@ 3 mg/dl. For CL: Salicylate @ 60 mg/dl. These represent typical interferents but will vary depending on the specific sensor technology used and the ionophores employed in those sensors.

Figure 17:
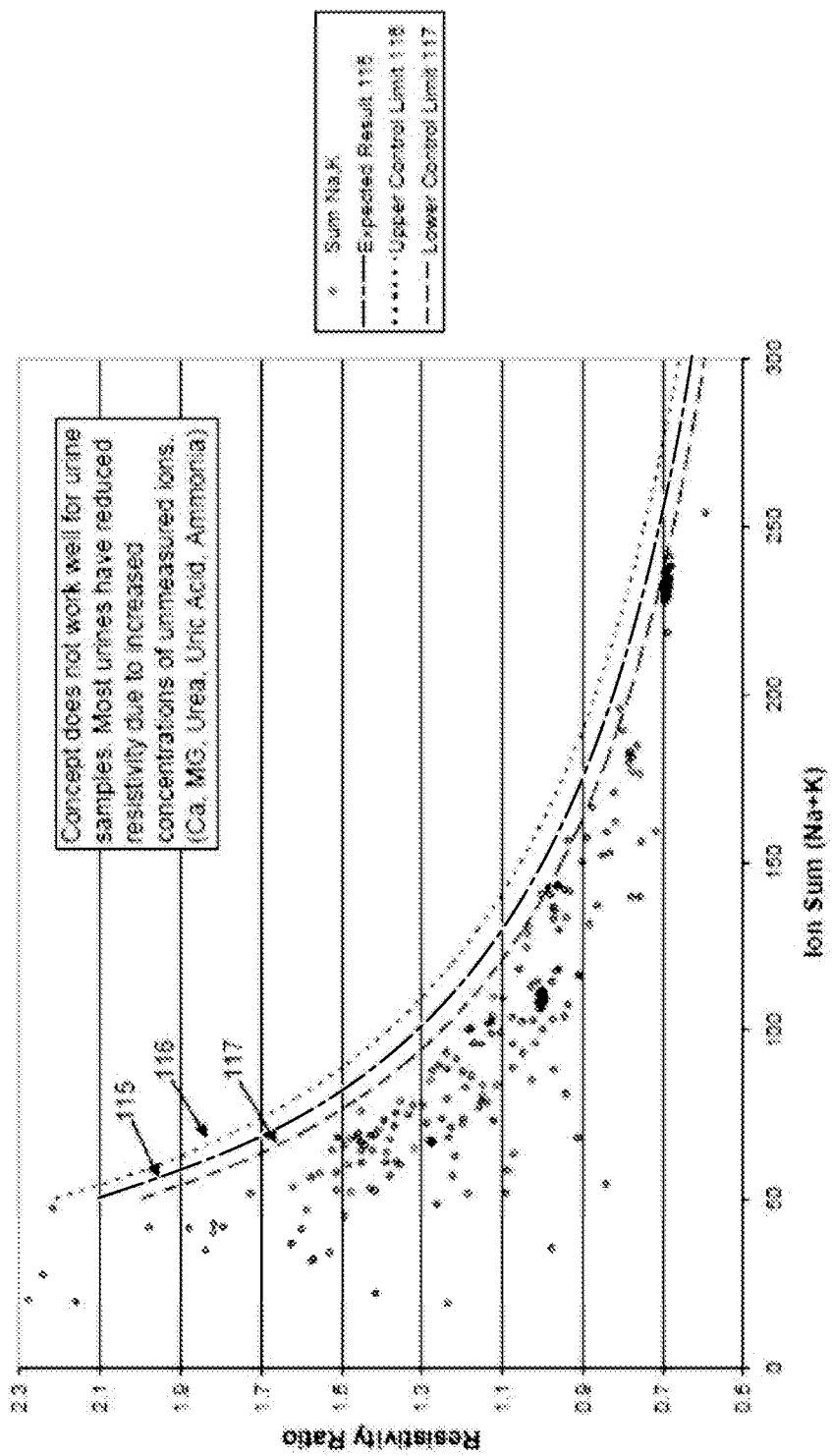
FIG. 17 is a plot showing an exemplary resistivity measurement.

FIG. 17 shows a plot of the electrolyte result verification for urine samples on an exemplary instrument. As shown in FIG. 17, the ion summation is plotted versus the resistivity ratio of the urine samples. FIG. 17 shows the ion summation for Na+K in relation to the expected results (shown by dashed line 115) and an upper control limit (shown by dashed line 116) and a lower control limit (shown by dashed line 117). As shown, the electrolyte result verification process does not work well for urine samples. A reason for this may be that most urines have reduced resistivity due to increased concentrations of unmeasured ions (e.g., CA, MG, Urea, Uric Acid, Ammonia, etc.). In order to more successfully use the present invention for urine samples, more of these other ions would need to be measured or otherwise accounted for.

In an alternate embodiment, the analysis may include an inverted resistivity ratio. In this embodiment, the relationship between Electrolyte Concentration and Resistivity Ratio is plotted. The following may represent the relationship between Electrolyte Concentration and Resistivity Ratio:

$$\text{Inverted Resistivity Ratio} = \frac{\text{Std A Resistivity}}{\text{Sample Fluid Resistivity}} = \frac{\text{Std A Liquid}}{\text{Fluid Verify}}$$

wherein electrolyte concentration=(Na+K+CL) or (Na+K).

Using the inverted resistivity ratio provides a linear relationship between electrolyte concentration and resistivity. Use of an inverted resistivity ratio also normalizes all measurements to the concentration of Standard A at the time of measurement on the specific instrument. The inverted resistivity ratio may be used for measurement error testing. Test 1 provided below, defined by equations (1), (2), and (3), compares the sum of the sodium and potassium concentrations against the fluid detection readings.

Test 1:

$$EV_{NAK} = E_1\left(\frac{StdAFluid}{SampleFluid}\right) + E_2 \quad (1)$$

$$EV_{NAK} = EV_{NAK} - (Na + K) \quad (2)$$

$$EV_{NAK} \begin{cases} > A_{NAK} \Rightarrow \text{Meas Error} \\ \leq A_{NAK} \Rightarrow \text{Good Result} \end{cases} \quad (3)$$

Test 2, defined by equations (4), (5), and (6), compares the sum of all three analytes (sodium, potassium, and chlorine) against the fluid detection reading. If Test 1 identifies a measurement error, then Test 2 is not performed.

Test 2:

$$EV_{NAKCL} = E_3\left(\frac{StdAFluid}{SampleFluid}\right) + E_4 \quad (4)$$

$$EV_{NAKCL} = EV_{NAKCL} - (Na + K + Cl) \quad (5)$$

$$EV_{NAKCL} \begin{cases} > A_{NAKCL} \Rightarrow \text{Meas Error} \\ \leq A_{NAKCL} \Rightarrow \text{Good Result} \end{cases} \quad (6)$$

$E_1$, $E_2$, $E_3$, $E_4$, $A_{NAK}$, and $A_{NAKCL}$ are constants, as defined below.
$E_1$=220.75
$E_2$=−70.86
$E_3$=454.55
$E_4$=−188.6
$A_{NAK}$=15.0
$A_{NAKCL}$=25.0

The following are variables from the current sample reading.
Na=concentration of the sodium;
K=concentration of the potassium;
Cl=concentration of the chlorine;
StdAFluid=fluid reading from the Std A Cycle (for the Std A reading taken after the sample reading); and
SampleFluid=fluid reading from the sample.

Figure 18:
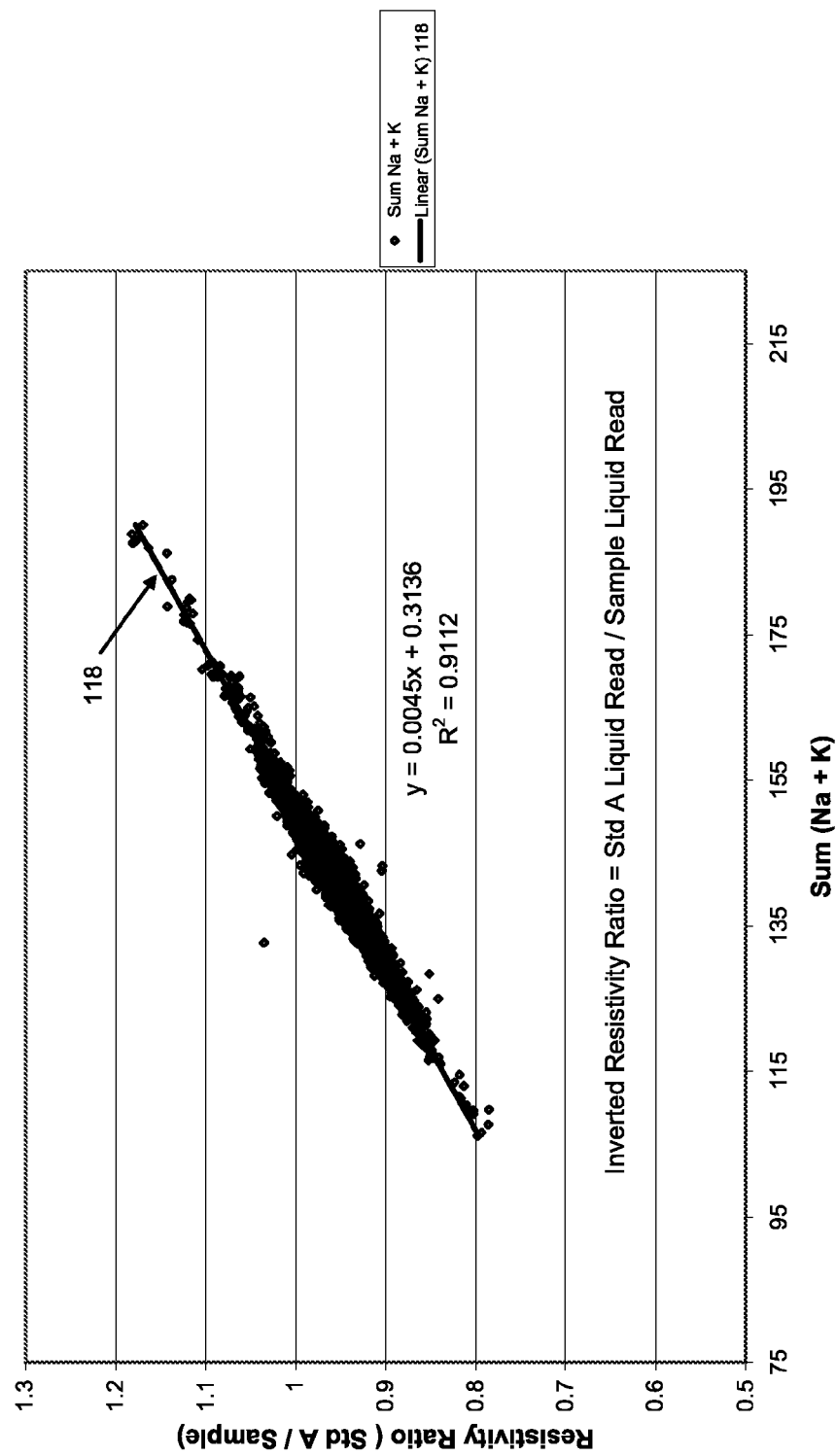
FIG. 18 is a plot showing an exemplary resistivity measurement.

FIG. 18 is a plot of the electrolyte result verification for patient samples. As shown in FIG. 18, the ion summation is plotted versus an inverted resistivity ratio of the samples for an exemplary instrument. In the illustrated example, the ion summation includes Na+K. The plot shows good correlation about the linear sum line 118 (e.g., fit Na+K).

Figure 19:
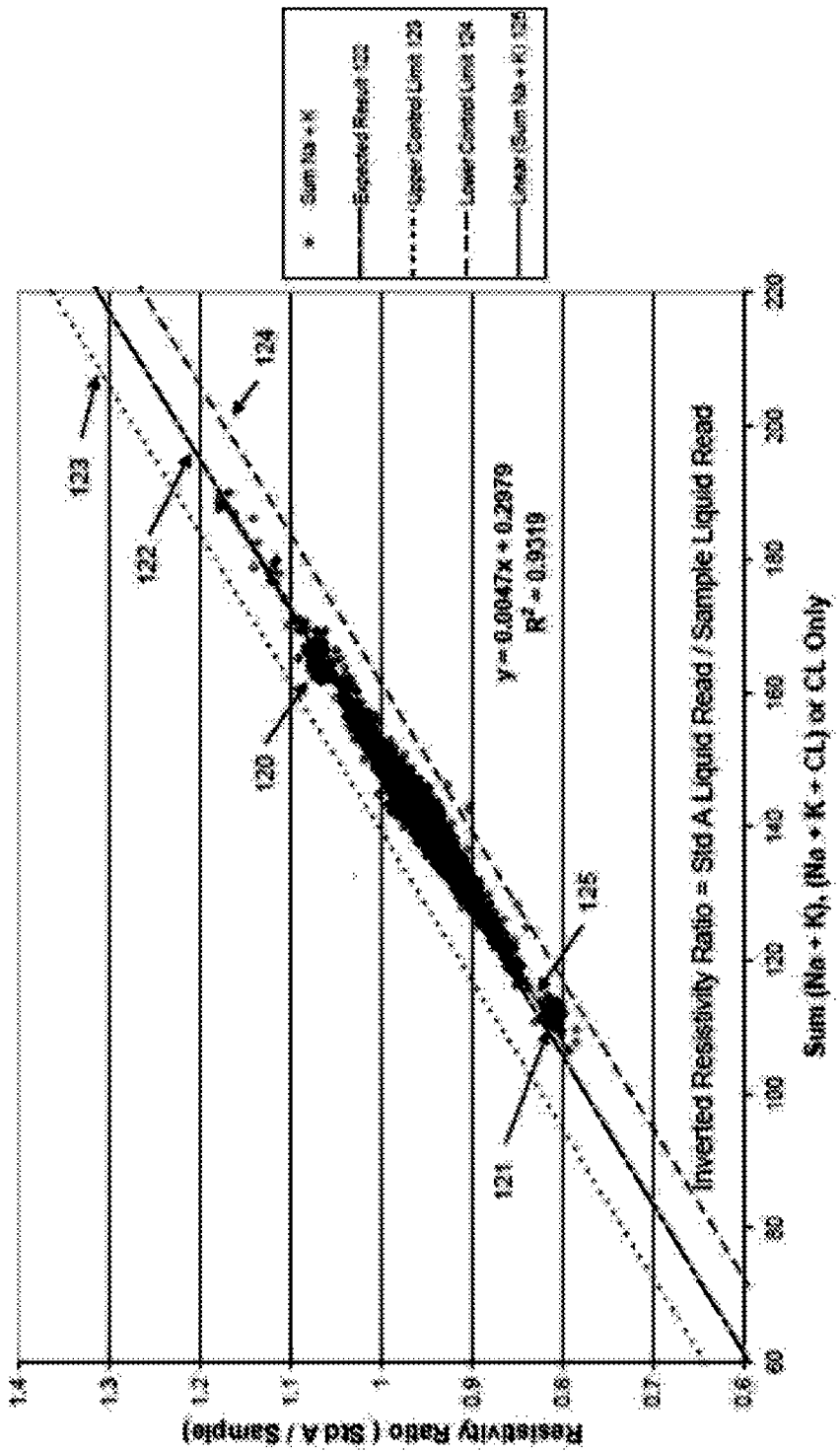
FIG. 19 is a plot showing an exemplary resistivity measurement.

FIG. 19 is a plot showing the results of FIG. 18 with the addition of high QC (quality control) samples 120 and low QC samples 121. As shown, the sample data groups well about the expected results 122, as illustrated by linear sum Na+K (line 125). The high QC and low QC further verify the measured results, and the results generally fit within an upper control limit (line 123) and lower control limit (line 124).

Figure 20:
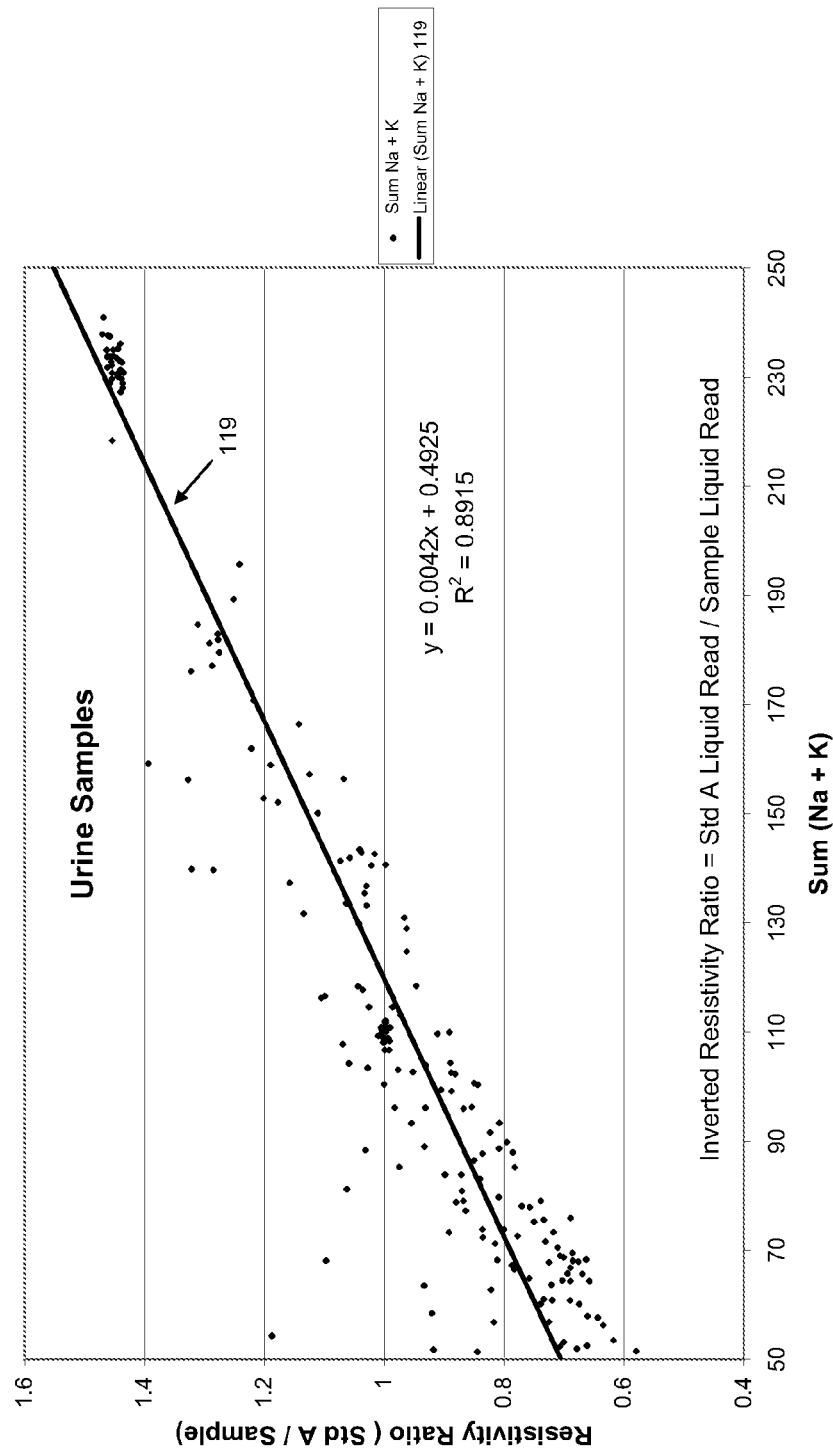
FIG. 20 is a plot showing an exemplary resistivity measurement.

FIG. 20 is a plot of the electrolyte result verification for urine samples. As shown in FIG. 20, the ion summation is plotted versus an inverted resistivity ratio of the urine samples for an exemplary instrument. In the illustrated example, the ion summation includes Na+K. The plot shows the relation of the measured resistivity to expected results shown by the linear line 119 (e.g., sum Na+K). Again, when only accounting to Na+K, the measured results do not correspond well to the expected response. This is due to other ions in the urine samples.

Figure 21:
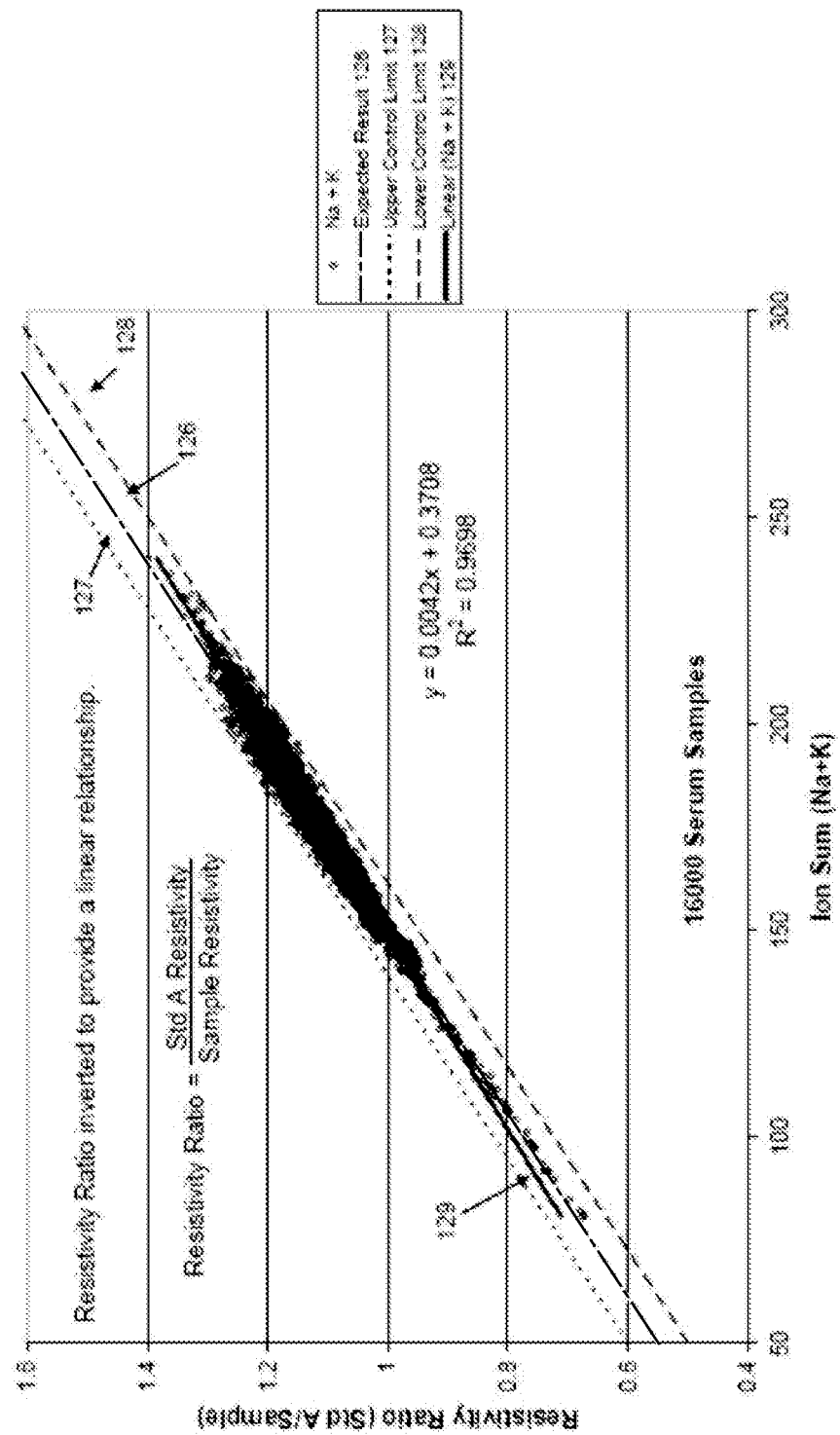
FIG. 21 is a plot showing an exemplary resistivity measurement.

FIG. 21 is a plot of the electrolyte result verification for the serum samples of FIG. 11 for the electrolyte concentration of Na+K. As shown in FIG. 21, the resistivity ratio from FIG. 11 has been inverted to show a linear relationship. The ion summation is plotted versus an inverted resistivity ratio of the serum samples. FIG. 21 shows the measured results about the expected results (shown by line 126) within an upper limit (shown by line 127) and a lower limit (shown by line 128). FIG. 21 also shows the linear sum (Na+K) (shown by line 129).

Figure 22:
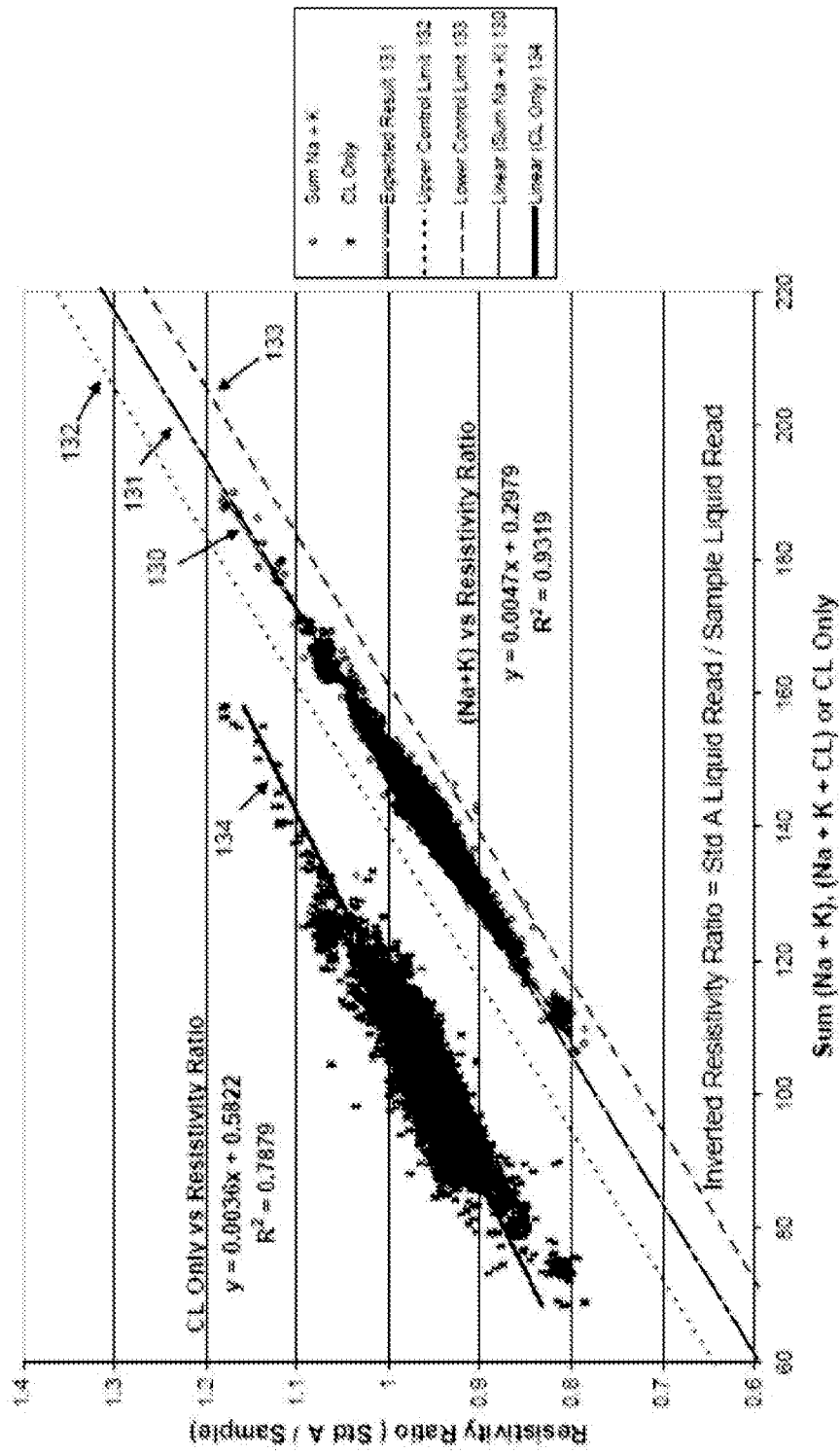
FIG. 22 is a plot showing an exemplary resistivity measurement.

FIG. 22 shows a plot of the ion summation versus inverted resistivity ratio and Cl only versus inverted resistivity ratio for an exemplary instrument. As illustrated in the electrolyte result verification plots shown in FIG. 22, the Cl only data is linear, but there is more scatter in these results as compared to the Na+K results. Line 130 presents the sum Na+K, and shows a good fit to the expected results (line 131). As shown, the data generally falls within an upper limit (line 132) is the lower limit (line 133). The linear sum (Cl only) is represented by line 134 for Cl only versus resistivity and is shown plotted with the sum Na+K data. This plot illustrates that the CL only results are not as accurate as the Na+K results, but could be used as a secondary means of verification. In such embodiments, a wider acceptance range may be needed for the upper and lower control limits.

Figure 23:
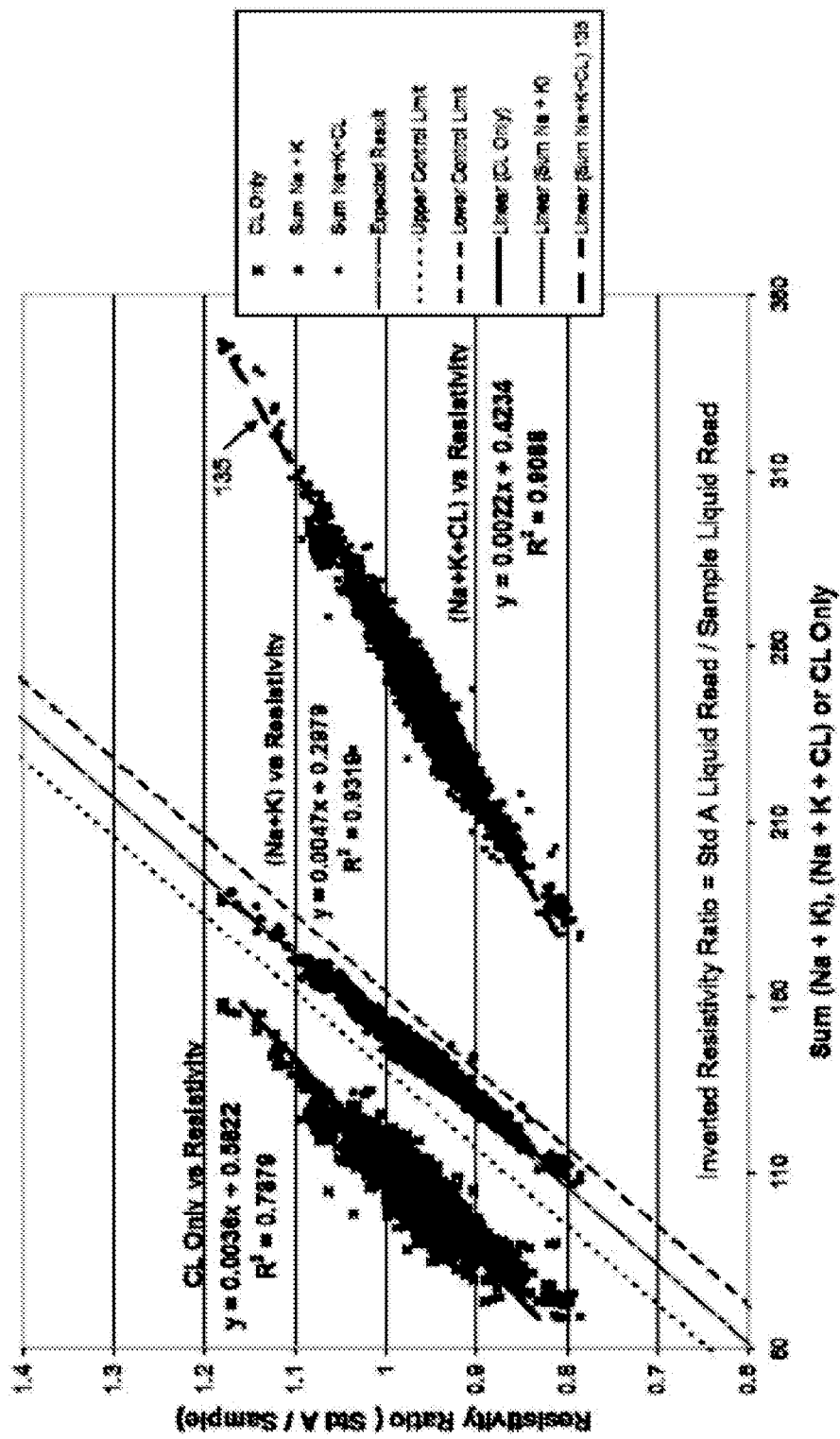
FIG. 23 is a plot showing an exemplary resistivity measurement.

FIG. 23 shows a similar relationship and graph as FIG. 22 with the additional options of Na+K+Cl shown as well. As shown, the linear sum (Na+K+Cl) is represented by line 135 for Na+K+Cl versus resistivity and is shown plotted with the Std A/Fluid data. This plot shows for Serum and Plasma samples the relative goodness of fit for each of the three possible ways to plot the data. The CL result would be better verified by the sum of Na+K+CL than CL only since it has a better R2 value. A different set of upper, lower and expected results could be generated for the Na+K+CL data. Na and K results would be better verified using the sum of Na+K.

The inverted resistivity ratio provides a linear response and simplifies implementation of electrolyte result verification into a clinical analyzer. For example, the plots of FIGS. 11-17 show that the ratio of sample resistivity over Standard A resistivity plotted against the summation of electrolyte concentration that the sensors measured in each sample has a clear relationship that as the electrolyte concentration increased the resistivity ratio decreased. The exact same data, however, just by inverting that ratio, as illustrated in FIGS. 18-23, produces a linear relationship. Linear relationships are typically easier to deal with, and hence preferred, especially when developing software to implement the electrolyte result verification solution.

When measured results do not correlate with an expected result (or theoretical result), or when measured results are outside an acceptable tolerance or range about the expected result, the instrument may respond in a number of ways. For example, the instrument response may be to: retry the measurement; purge and cycle the sample fluid and then make new measurement; generate an error; record an error; retry the measurement; indicate an alarm; flag the result; initiate an automated recovery (e.g., priming and/or cleaning), or the like.

The acceptable tolerance may be defined by an upper range (or limit) and a lower range (or limit). These limits can be based on a statistical analysis of a large number of normal patient samples run on several instruments. A linear fit of this data can produce the expected result equation and the standard error of the fit can be used to calculate upper and lower control limits. Another method would be to use the same fit of the data above, but use an upper and lower limit based on the clinical significance of the methods. For Na and K this is often described as +/−5 mmol/L and +/−0.2 mmol/L. In this embodiment, the upper and lower control limits would be set at +/−5.2 mmol away from the expected result line.

Embodiments of the electrolyte result verification may be implemented on new instruments. Embodiments of the invention may be implemented via software in new clinical analyzers. Embodiments of the electrolyte result verification may be retrofit on existing instruments. Other embodiments of the invention may be implemented via software upgrades in existing clinical analyzers.

Instrument as used herein means a medical device or equipment used for medical purposes to diagnosis patient samples. Instrument as used herein includes a clinical analyzer. Some instruments are used for veterinary labs and would also work with embodiments of the present invention. Patients could include most animals.

As used herein, sample includes, but is not limited to, a solution to be analyzed. As sample may include aqueous standards and verifiers, control products (e.g., protein matrix), plasma, serum, and/or urine.

An electrolyte, as used herein, includes any substance containing free ions that make the substance electrically conductive. The most typical electrolyte is an ionic solution. Measurement of electrolytes is a commonly performed diagnostic procedure, performed via blood testing with ion selective electrodes or urinalysis by medical technologists. Electrolytes measured most often include sodium ($Na^+$), potassium ($K^+$), and chloride ($Cl^-$). Solutions of primary focus here include samples comprising bodily fluids (e.g., blood serum and plasma).

As used herein, resistivity is a measure of how strongly a sample opposes the flow of electric current. A low resistivity indicates a sample that readily allows the movement of electric charge. A high resistivity indicates a sample that does not readily allow the movement of electric charge.

Although the embodiments of the invention are primarily described with respect to sample resistivity measurements, the invention is not so limited and it is contemplated that the invention could also be described with respect to the sample conductivity measurements. As one of ordinary skill would recognize, conductivity and resistivity are both measures of the ability of a fluid to conduct electrical current. Conductivity is simply the reciprocal or inverse of resistivity—i.e., conductivity=1/resistivity.

Embodiments of the present invention provide improvements over conventional clinical analyzers in that in addition to simply using the liquid/air detect circuit to determine the presence of liquid or air in the channel of to the sensor cartridge, the present invention allows for more precise utilization of the resistivity measurement to determine a relative difference between two fluids—an unknown sample and a Standard. A comparison of the measured resistivity to an expected resistivity allows for the verification of the sample electrolyte results.

Embodiments of the present invention may also be used to verify proper flow and/or the presence of small bubbles, which could affect the measured electrolyte results. Embodiments of the present invention may be used for dialysis patients, cancer treatment patients, and the like. Embodiments of the present invention may be used by veterinary hospitals for most animals. Different limits and expected results may be necessary for different species. Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims cover be construed to all such equivalent variations as fall within the true spirit and scope of the invention.

What is claimed is:

1. A sample resistivity measurement system for sample electrolyte result verification comprising:
    a sample cartridge for performing sample electrolyte measurements, said sample cartridge comprising:
        one or more ion selective electrodes;
        a common reference electrode to provide a constant reference potential;
        a circuit connecting each of said one or more ion selective electrodes with said reference electrode;
        an electrometer connected to said circuit to measure a potential of said one or more ion selective electrodes against said reference electrode;
        wherein concentrations of desired ions are calculated from an electrode voltage difference between a sample having unknown ion concentration and unknown resistivity and a standard solution having known ion concentration and known resistivity to obtain a measured sample electrolyte result, wherein said sample and said standard solution are run alternately in series through said sample cartridge;
    a measured sample resistivity of said sample;
    a measured sample resistivity of said standard solution used to establish a response slope for said one or more ion-selective electrodes and to provide a reference point against which said sample is compared;
    a resistivity ratio calculated from said measured sample resistivity of said sample and said measured sample resistivity of said standard solution;
    historical data comprising one or more of: measured sample electrolyte concentrations, and measured sample resistivities;
    an expected sample resistivity response developed from said historical data; and
    a tolerance about said expected sample resistivity response, wherein said measured sample electrolyte result is verified to be an acceptable result if said measured sample resistivity falls within said tolerance about said expected sample resistivity response.

2. The system of claim 1, further comprising a flag triggered when said measured sample resistivity falls outside said tolerance.

3. The system of claim 1, wherein said system provides a separate and quantitative means for verification of measured sample electrolyte results of an electrolyte measuring module on a clinical chemistry analyzer.

4. The system of claim 1, wherein said system performs said sample resistivity measurement on each sample run through said sample cartridge to detect errors in individual electrolyte result calculations.

5. The system of claim 1, further comprising:
    an integrated multi-sensor technology (IMT) comprising said ion selective electrodes (ISE), wherein said sample cartridge is inserted in said IMT for receipt and measurement of said sample and said standard solution;
    a database storing said historical data of measured sample electrolyte concentrations; and
    a processor connected to said IMT to perform said calculation of ion concentration and connected to said database to determine whether said measured sample resistivity falls within said tolerance.

6. The system of claim 1, wherein a relationship between electrolyte concentration and resistivity ratio is represented by a ratio of said measured sample resistivity over said measured standard solution resistivity, which provides a power relationship between electrolyte concentration and resistivity.

7. The system of claim 1, wherein a relationship between electrolyte concentration and resistivity ratio is represented by a ratio of said measured standard solution resistivity over said measured sample resistivity, which provides a linear relationship between electrolyte concentration and resistivity.

8. The system of claim 7, wherein the relationship is compared against a first constant, wherein if the relationship is greater than the first constant, the measured sample resistivity comprises a measurement error, and wherein if the relationship is greater than or equal to the first constant, the measured sample resistivity comprises a good result.

9. The system of claim 8, wherein the relationship is compared against a second constant, wherein if the relationship is greater than the second constant, the measured sample resistivity comprises a measurement error, and wherein if the relationship is greater than or equal to the second constant, the measured sample resistivity comprises a good result.

10. The system of claim 9, wherein the relationship further comprises a function of a concentration of one or more of sodium (Na), potassium (K), and chlorine (Cl).

11. The system of claim 1, wherein said tolerance further comprises an upper limit and a lower limit determined from said historical data.

12. The system of claim 1, further comprising a plot comprising:
    an x-axis comprising a summation of ions;
    a y-axis comprising said resistivity ratio of said resistivity measurements;
    an expected sample resistivity response curve plotted using said expected sample resistivity response;
    a tolerance curve plotted using said tolerance, said tolerance curve plotted about said expected sample resistivity response curve; and
    measured sample resistivity points, said measured sample resistivity points plotted on said plot relative to said expected sample resistivity response curve and said tolerance curve.

13. The system of claim 1, wherein said one or more ion-selective electrodes further comprise one or more of: a sodium (Na) electrode, a potassium (K) electrode, and a chlorine (Cl) electrode; for measuring said one or more desired ions comprising: sodium (Na), potassium (K), and chlorine (Cl), respectively.

14. The system of claim 1, wherein said sample comprises patient serum and plasma samples and includes a measurement of: sodium (Na) ions and potassium (K) ions; to verify an electrolyte measurement of sodium (Na) and potassium (K).

15. The system of claim 1, wherein said sample comprises patient serum and plasma samples and includes a measurement of: sodium (Na) ions, potassium (K) ions, and chlorine (Cl) ions; to verify an electrolyte measurement of sodium (Na), potassium (K), and chlorine (Cl).

16. The system of claim 1, wherein said sample comprises patient serum and plasma samples and includes a measurement of: sodium (Na) ions and potassium (K) ions; and sodium (Na) ions, potassium (K) ions, chlorine (Cl) ions; to isolate and verify an electrolyte measurement of chlorine (Cl).

17. A method for using patient sample resistivity for patient sample electrolyte result verification, said method comprising:
- running a patient sample having an unknown resistivity and measuring a resistivity of said patient sample;
- running a standard solution having a known resistivity and measuring a resistivity of said standard solution to provide a reference point against which said patient sample may be compared;
- calculating a resistivity ratio comprising said measured patient sample resistivity over said measured standard solution resistivity;
- comparing said measured patient sample resistivity to an expected resistivity derived from historical data of previously measured patient sample resistivity; and
- flagging said unknown patient sample if said measured unknown patient sample resistivity does not fall within a predefined tolerance about said expected resistivity.

18. A method for verifying patient sample electrolyte results using patient sample resistivity measurements, said method comprising:
- providing a sensor cartridge comprising:
  - one or more ion-selective electrodes;
  - a common reference electrode to provide a constant reference potential;
  - a circuit connecting each of said one or more ion-selective electrodes with said reference electrode;
  - an electrometer connected to said circuit to measure a potential of said one or more ion-selective electrodes against said reference electrode;
- running a patient sample through said sensor cartridge;
- measuring a concentration of a desired ion in said patient sample using one or more ion-selective electrodes;
- measuring a resistivity of said patient sample using an electrometer connected to said circuit connecting said one or more ion-selective electrodes and said reference electrode, wherein said electrometer measures a potential of said one or more ion-selective electrodes against said reference electrode;
- running a standard solution through said sensor cartridge;
- measuring a concentration of said desired ion in said standard solution using said one or more ion-selective electrodes;
- measuring a resistivity of said standard solution to calibrate a slope response of said one or more ion-selective electrodes and to provide a reference point against which said patient sample is compared;
- calculating a concentration of said desired ion from said comparison said measured concentration of said desired ion in said patient sample and said measured concentration of said desired ion in said standard solution;
- calculating a resistivity ratio comprising said measured patient sample resistivity divided by said measured standard solution resistivity;
- comparing said measured patient sample resistivity to an expected resistivity developed from historical resistivity measurements of other patient samples; and
- flagging said measured patient sample if said measured patient sample resistivity does not fall within a predefined tolerance about said expected resistivity.

19. The method of claim 18, further comprising:
- plotting a summation of ions along an x-axis and said resistivity ratio along a y-axis;
- plotting an expected sample resistivity response curve comprising said historical resistivity measurements;
- plotting a tolerance curve using said predefined tolerance, said tolerance curve plotted about said expected sample resistivity response curve; and
- plotting said measured sample resistivity relative to said expected sample resistivity response curve and said tolerance curve.

20. The method of claim 18, wherein said patient sample comprises patient serum and plasma samples, and wherein said desired ion comprises one or more of: sodium (Na), potassium (K), and chlorine (Cl); to verify an electrolyte measurement of sodium (Na), potassium (K), and chlorine (Cl).

21. The method of claim 18, wherein said patient sample comprises patient serum and plasma samples, and wherein said desired ion comprises one or more of: sodium (Na) ions and potassium (K) ions; to verify an electrolyte measurement of sodium (Na) and potassium (K).

22. The method of claim 18, wherein said patient sample comprises patient serum and plasma samples, and wherein said desired ion comprises one or more of: sodium (Na) ions, potassium (K) ions, and chlorine (Cl) ions; to verify an electrolyte measurement of sodium (Na), potassium (K), and chlorine (Cl).

23. The method of claim 18, wherein said patient sample comprises patient serum and plasma samples, and wherein said desired ion comprises one or more of: sodium (Na) ions and potassium (K) ions; and sodium (Na) ions, potassium (K) ions, chlorine (Cl) ions; to isolate and verify an electrolyte measurement of chlorine (Cl).

* * * * *